(12) United States Patent
Nishihara et al.

(10) Patent No.: US 10,063,784 B2
(45) Date of Patent: *Aug. 28, 2018

(54) IMAGING APPARATUS, AN ELECTRONIC DEVICE, AND IMAGING METHOD TO UNIFORMIZE DISTRIBUTION OF INCIDENT LIGHT, AND A PHOTOSTIMULATED LUMINESCENCE DETECTION SCANNER

(71) Applicant: SONY SEMICONDUCTOR SOLUTIONS CORPORATION, Kanagawa (JP)

(72) Inventors: Toshiyuki Nishihara, Kanagawa (JP); Hirofumi Sumi, Kanagawa (MY)

(73) Assignee: SONY SEMICONDUCTOR SOLUTIONS CORPORATION, Kanagawa (JP)

( * ) Notice: Subject to any disclaimer, the term of this patent is extended or adjusted under 35 U.S.C. 154(b) by 36 days.

This patent is subject to a terminal disclaimer.

(21) Appl. No.: 15/249,654

(22) Filed: Aug. 29, 2016

(65) Prior Publication Data

US 2016/0366322 A1 Dec. 15, 2016

Related U.S. Application Data

(63) Continuation of application No. 14/362,313, filed as application No. PCT/JP2012/081257 on Dec. 3, 2012, now Pat. No. 9,462,190.

(30) Foreign Application Priority Data

Dec. 9, 2011 (JP) ................................. 2011-270240

(51) Int. Cl.
*H01L 27/146* (2006.01)
*H04N 5/235* (2006.01)
(Continued)

(52) U.S. Cl.
CPC ......... *H04N 5/2351* (2013.01); *G01N 21/645* (2013.01); *G01T 1/2018* (2013.01);
(Continued)

(58) Field of Classification Search
CPC ................ G01N 21/645; G01T 1/2018; H01L 27/14658; H01L 27/14625;
(Continued)

(56) References Cited

U.S. PATENT DOCUMENTS

| 6,741,341 B2* | 5/2004 | DeFlumere ............. F41G 7/008 250/203.6 |
| 7,301,608 B1 | 11/2007 | Mendenhall et al. |
| 2015/0226865 A1 | 8/2015 | Nishihara et al. |

FOREIGN PATENT DOCUMENTS

| JP | 2000-358198 A | 12/2000 |
| JP | 2004-532998 A | 10/2004 |
| JP | 2011-097581 A | 5/2011 |

* cited by examiner

*Primary Examiner* — Que T Le
(74) *Attorney, Agent, or Firm* — Chip Law Group

(57) ABSTRACT

An object is to improve accuracy of photon counting in an imaging apparatus.

The imaging apparatus includes a light uniformizing unit. The light uniformizing unit included in the imaging apparatus substantially uniformizes distribution of photons in an orthogonal direction toward an optical axis of incident light, which is incident to an imaging element in the imaging apparatus and the number of photons of which is to be detected, a plurality of pixels being arranged to the imaging element. The light uniformizing unit supplies the uniformized light to the imaging element to which a plurality of pixels are arranged in the imaging apparatus.

20 Claims, 20 Drawing Sheets

(51) Int. Cl.

| | |
|---|---|
| *H04N 5/32* | (2006.01) |
| *H04N 5/361* | (2011.01) |
| *H04N 5/378* | (2011.01) |
| *G01N 21/64* | (2006.01) |
| *G01T 1/20* | (2006.01) |
| *H04N 5/374* | (2011.01) |
| *H04N 5/225* | (2006.01) |

(52) U.S. Cl.
CPC .. *H01L 27/14625* (2013.01); *H01L 27/14643* (2013.01); *H01L 27/14658* (2013.01); *H04N 5/2254* (2013.01); *H04N 5/2353* (2013.01); *H04N 5/32* (2013.01); *H04N 5/361* (2013.01); *H04N 5/374* (2013.01); *H04N 5/378* (2013.01)

(58) Field of Classification Search
CPC ............ H01L 27/14643; H04N 5/2351; H04N 5/2353; H04N 5/32
USPC .................................. 250/208.1, 239, 214 R
See application file for complete search history.

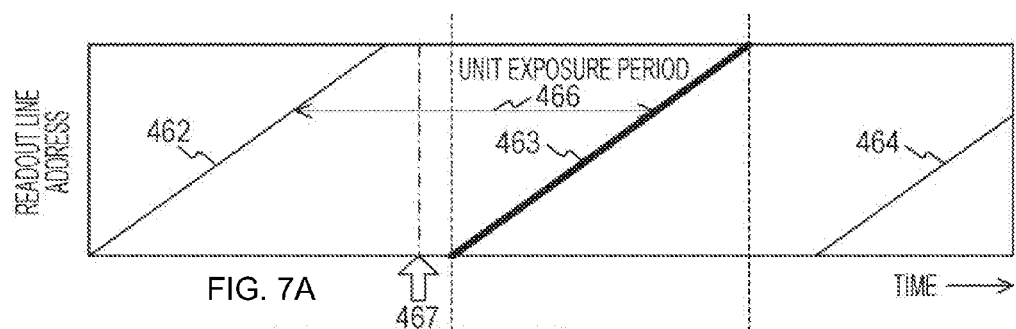
FIG. 7A
FIG. 7B
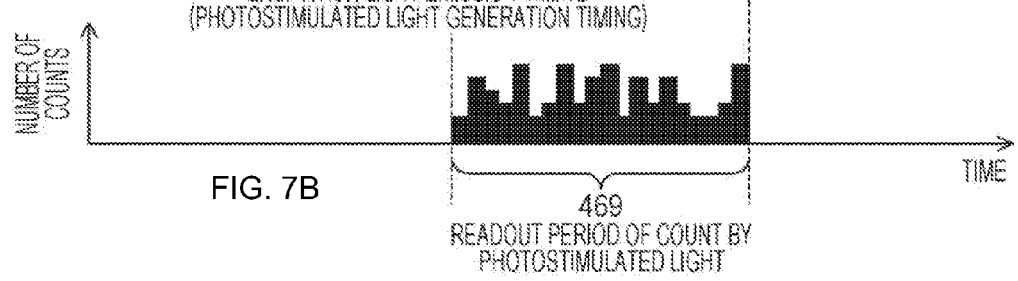
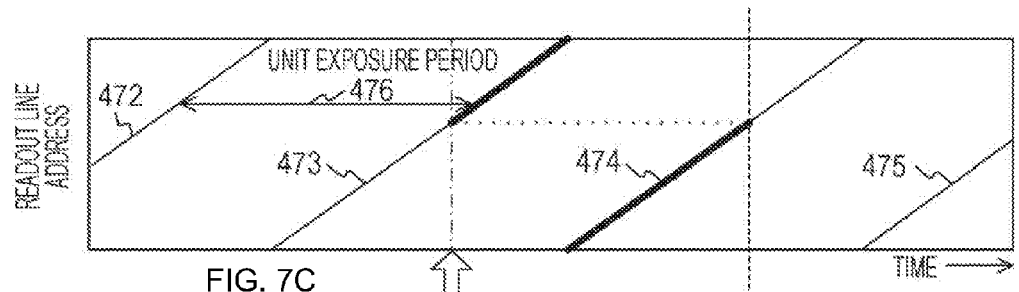
FIG. 7C
FIG. 7D
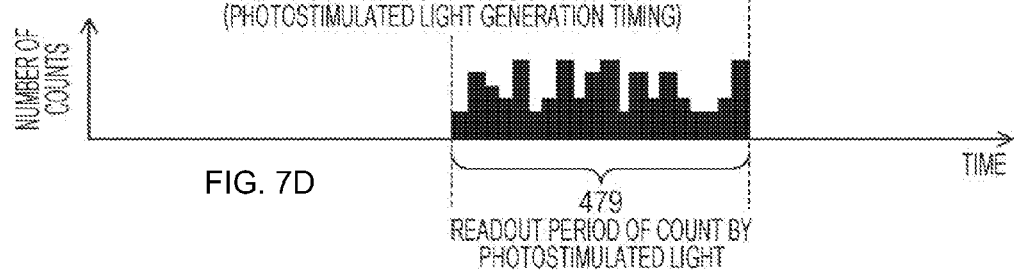

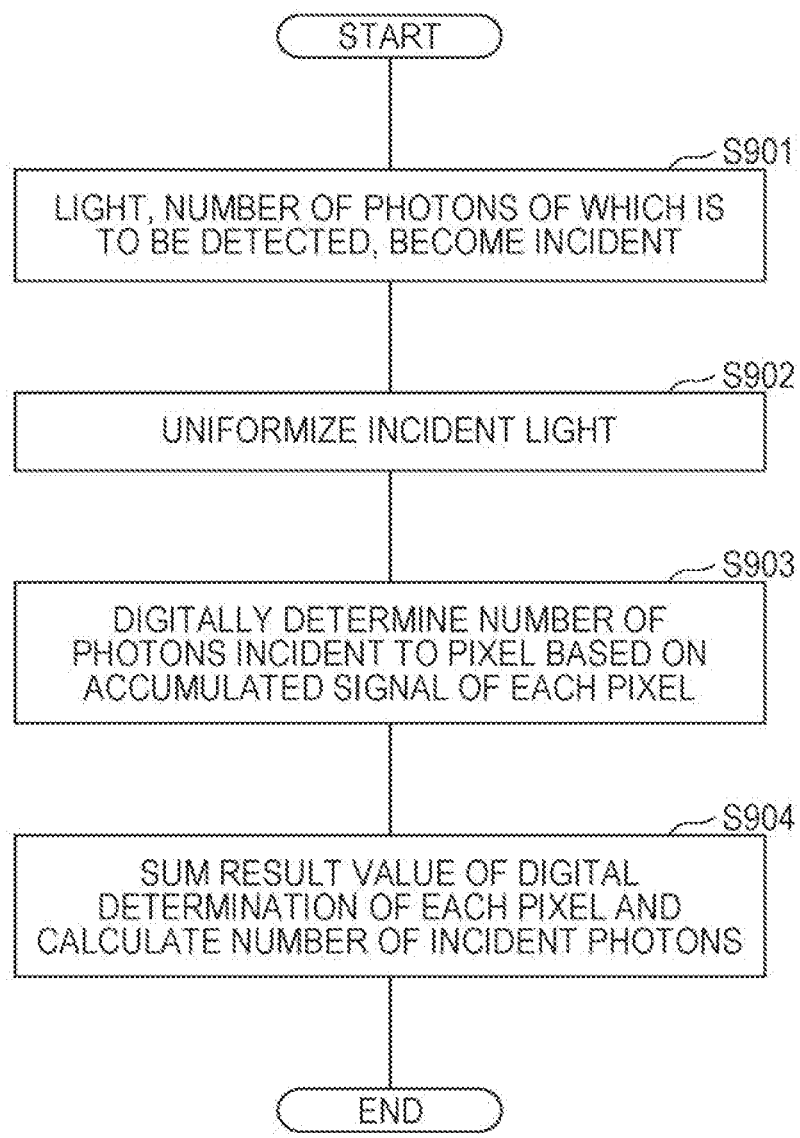

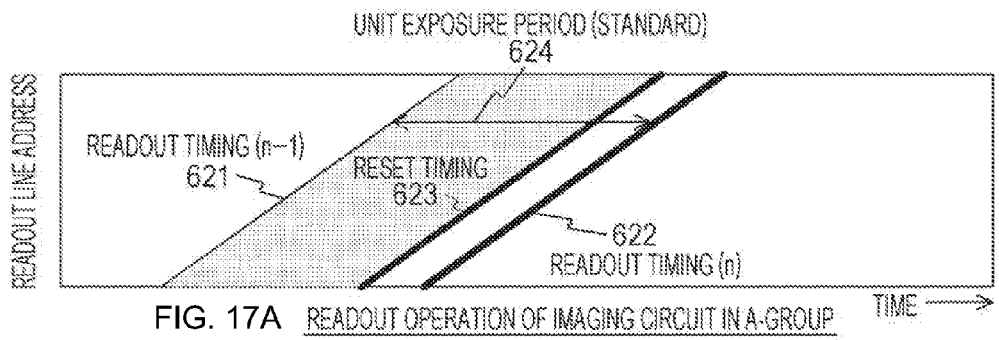
FIG. 17A  READOUT OPERATION OF IMAGING CIRCUIT IN A-GROUP
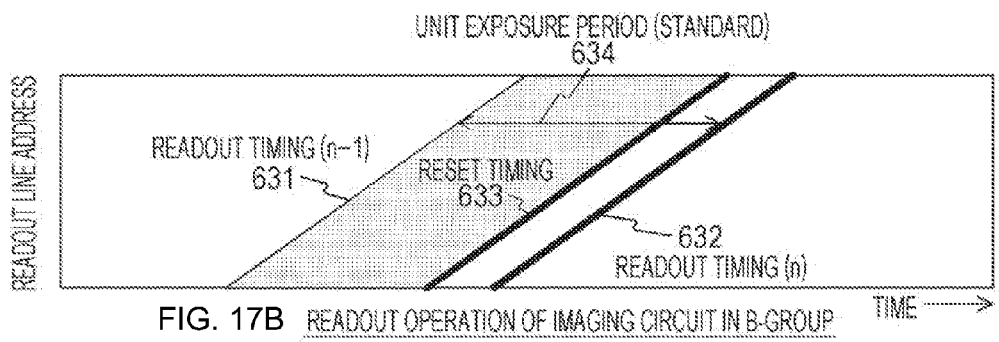
FIG. 17B  READOUT OPERATION OF IMAGING CIRCUIT IN B-GROUP
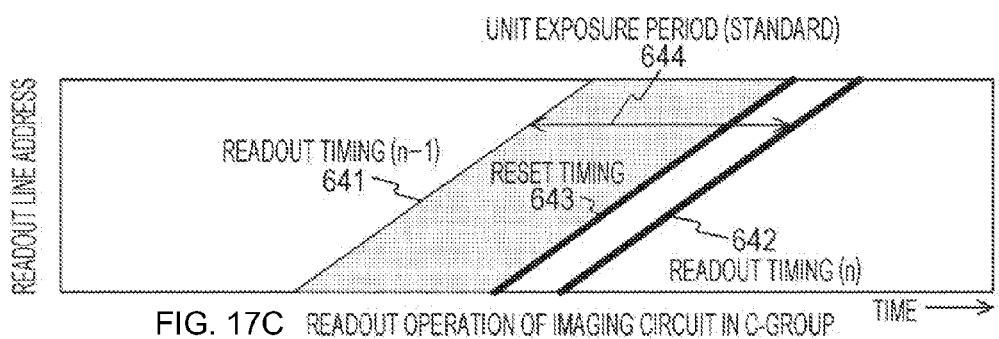
FIG. 17C  READOUT OPERATION OF IMAGING CIRCUIT IN C-GROUP
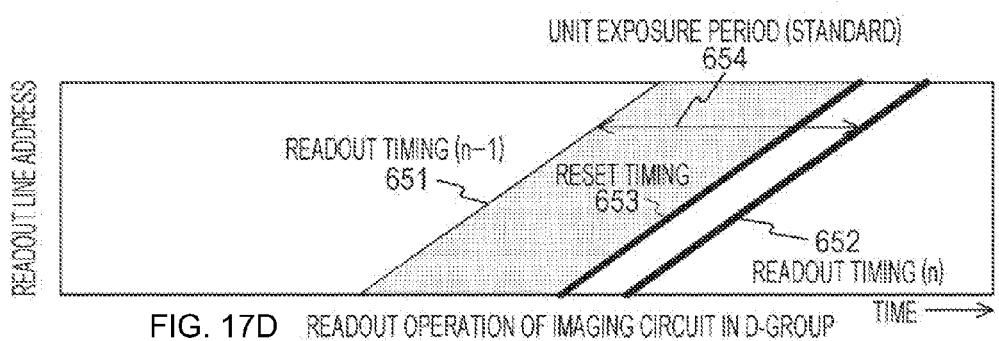
FIG. 17D  READOUT OPERATION OF IMAGING CIRCUIT IN D-GROUP

IMAGING APPARATUS, AN ELECTRONIC DEVICE, AND IMAGING METHOD TO UNIFORMIZE DISTRIBUTION OF INCIDENT LIGHT, AND A PHOTOSTIMULATED LUMINESCENCE DETECTION SCANNER

CROSS REFERENCE TO RELATED APPLICATIONS

The present disclosure is a continuation of U.S. patent application Ser. No. 14/362,313 filed in USPTO on Jun. 2, 2014 which is a National Phase Patent Application of International Application No. PCT/JP2012/081257 filed on Dec. 3, 2012 which claims priority from Japanese Priority Patent Application JP 2011-270240 filed in the Japan Patent Office on Dec. 9, 2011. Each of the above referenced applications is hereby incorporated by reference in its entirety.

TECHNICAL FIELD

The present technique relates to an imaging apparatus. Specifically, the present technique relates to an imaging apparatus including an imaging element to detect weak light, an electronic device including the imaging apparatus, and an imaging method.

BACKGROUND ART

Recently, an apparatus to detect weak light has been widely introduced centering on a medical site and a research site. In such an apparatus, a photomultiplier tube which is relatively expensive is used as a detection unit of weak light.

Also, instead of the photomultiplier tube, an apparatus to detect weak light by using a complementary metal oxide semiconductor (CMOS) image sensor, which can be produced at a low price, is proposed (see, for example, Patent Document 1).

CITATION LIST

Patent Document

Patent Document 1: JP 2011-97581 A

SUMMARY OF THE INVENTION

Problems to be Solved by the Invention

In the conventional technique, weak light is detected by counting (photon counting) the number of photons incident to each pixel of an CMOS image sensor.

In this manner, when the number of photons incident to each pixel is counted for each pixel, it is important to supply, to each pixel, the light suitable for photon counting and to improve accuracy of the photon counting.

In consideration of such a condition, the present technique has been made to improve accuracy of photon counting.

Solutions to Problems

The present technique has been made to solve the problems above, and a first aspect thereof is an imaging apparatus including a light uniformizing unit configured to substantially uniformize distribution of incident light, which is incident to an imaging element and the number of photons of which is to be detected, in an orthogonal direction toward an optical axis and to supply the uniformized light to the imaging element, a plurality of pixels being arranged to the imaging element. Thus, incident light, the number of photons of which is to be detected, is substantially uniformized and the uniformized light becomes incident to an imaging element.

Also, in the first aspect, the imaging element performs digital determination in respect to the number of incident photons of the uniformized light supplied to each of the plurality of pixels and outputs a determination result value of the digital determination of each of the plurality of pixels, and a calculation unit configured to sum the output determination result values of the plurality of pixels by a frame as a unit and to calculate, based on the summed value, the number of photons of the incident light in an exposure period of the frame may be further included. Thus, digital determination is performed on each pixel to determine the number of incident photons of uniformized light and the number of photons of the incident light is calculated based on a summed value in which the determination result values of the digital determination are summed by a frame as a unit.

Also, in the first aspect, the calculation unit may calculate the number of photons of the incident light, based on the summed value, by using difference correction information indicating a relationship between the number of photons actually incident to the plurality of pixels and the summed value. Thus, the number of photons of incident light is calculated based on a summed value by using difference correction information indicating a relationship between the number of photons actually incident to a plurality of pixels and the summed value.

Also, in the first aspect, the imaging element may perform binary determination as the digital determination, and the calculation unit may perform the calculation by using information, which is related to Poisson distribution or a relationship approximate to the Poisson distribution, as the difference correction information. Thus, the number of photons of incident light is calculated based on a summed value by using information related to Poisson distribution or a relationship approximate to the Poisson distribution.

Also, in the first aspect, based on pixel positional information to identify a pixel having high dark current among the plurality of pixels, the calculation unit may eliminate the determination result value of the pixel having high dark current and may calculate the summed value. Thus, based on pixel positional information to identify a pixel having high dark current among a plurality of pixels, a summed value is calculated with a determination result value of the pixel having high dark current being eliminated.

Also, in the first aspect, the calculation unit may correct the summed value based on a ratio of the number of pixels, the determination result values of which are eliminated, to the total number of pixels. Thus, a summed value is corrected based on a ratio of the number of pixels, determination result values of which are eliminated, to the total number of pixels.

Also, in the first aspect, the imaging element may perform binary determination as the digital determination, and the calculation unit may calculate the number of photons of the incident light, based on the corrected summed value, by using differential information related to Poisson distribution or a relationship approximate to the Poisson distribution. Thus, a summed value which is corrected based on a ratio of the number of pixels, determination result values of which are eliminated, to the total number of pixels is further corrected by using differential information to calculate the number of photons.

Also, in the first aspect, the imaging element may include a plurality of pixel arrays, each of which is driven independently, and the light uniformizing units may be respectively provided to and paired with the plurality of pixel arrays. Thus, a plurality of imaging units, in each of which a pair of a light uniformizing unit and a pixel array is provided, is provided to an imaging element.

Also, in the first aspect, a dividing unit configured to substantially uniformize distribution of the incident light in an orthogonal direction of an optical axis and to divide the uniformized incident light into a plurality of pieces of incident light may be further included, and the light uniformizing unit may supply, to the pixel array paired therewith, the incident light divided into a plurality of pieces. Thus, the uniformized incident light is divided into pieces and the divided pieces of the light are respectively supplied to imaging units in each of which a pair of a light uniformizing unit and a pixel array is provided.

Also, in the first aspect, the plurality of pixel arrays may have same length and same start timing of exposure periods, and each of the plurality of pixel arrays may perform digital determination in respect to the number of incident photons of the light supplied to each of the plurality of pixels in the pixel array and may output a determination result value of the digital determination of each of the plurality of pixels, and the calculation unit configured to sum the output determination result values of the plurality of pixels by an exposure period as a unit, and to calculate, based on the summed value, the number of photons of the incident light in the exposure period may be further included. Thus, a plurality of imaging units, in each of which a pair of a light uniformizing unit and a pixel array is provided, is driven at the same timing and a value, in which summed values in the plurality of imaging units are summed, is calculated as a summed value in an exposure period.

Also, in the first aspect, the plurality of pixel arrays may be separated into a plurality of groups having different start timing of exposure periods, and each of the plurality of pixel arrays may perform digital determination in respect to the number of incident photons of the light supplied to each of the plurality of pixels in the pixel array and may output a determination result value of the digital determination of each of the plurality of pixels, and the calculation unit configured to sum the output determination result values of the plurality of pixels by a group as a unit, to correct the summed value based on a ratio of the number of pixel arrays which belong to the group related to the summed value to the total number of pixel arrays, and to calculate, based on the corrected summed value, the number of photons of the incident light in an exposure period of the group may be further included. Thus, a plurality of imaging units is separated into a plurality of groups and a summed value in an exposure period of each group is calculated based on summed values generated by the imaging units which belong to the group.

Also, a second aspect of the present technique is an electronic device including: a light uniformizing unit configured to substantially uniformize distribution of incident light, which is incident to an imaging element and the number of photons of which is to be detected, in an orthogonal direction toward an optical axis of the incident light and to supply the uniformized light, a plurality of pixels being arranged to the imaging element; the imaging element configured to perform digital determination on each of the plurality of pixels in respect to the number of incident photons of the supplied light and to output a determination result value of the digital determination of each of the plurality of pixels; and a calculation unit configured to sum the output determination result values of the plurality of pixels by a frame as a unit and to calculate, based on the summed value, the number of photons of the incident light in an exposure period of the frame. Thus, incident light, the number of photons of which is to be detected, is substantially uniformized and made incident to an imaging element, and photon counting is performed based on the uniformized light.

Also, a third aspect of the present technique is a photostimulated luminescence detection scanner including a detection unit which includes a plurality of imaging units, each of the imaging unit including: a light uniformizing unit configured to substantially uniformize distribution of incident light, the number of photons of which is to be detected, in an orthogonal direction toward an optical axis and to supply the uniformized light; and an imaging element configured to perform digital determination on each of the plurality of pixels in respect to the number of incident photons of the supplied light and to output a determination result value of the digital determination of each of the plurality of pixels. Thus, incident light, the number of photons of which is to be detected, is substantially uniformized and made incident to an imaging element, and photon counting is performed based on the uniformized light.

Also, a fourth aspect of the present technique is an imaging method including: a light uniformizing step to substantially uniformize distribution of incident light, which is incident to an imaging element and the number of photons of which is to be detected, in an orthogonal direction toward an optical axis of the incident light and to supply the uniformized light to the imaging element, a plurality of pixels being arranged to the imaging element; a determination step to perform digital determination on each of the plurality of pixels in respect to the number of incident photons of the light supplied to each of the plurality of pixels; and a calculation step to sum the determination result values of the plurality of pixels by a frame as a unit and to calculate, based on the summed value, the number of photons of the incident light in an exposure period of the frame. Thus, incident light, the number of photons of which is to be detected, is substantially uniformized and made incident to an imaging element, and the number of photons, of the uniformized light, received by each pixel is digitally determined. Then, determination result values of the determination are summed by a frame as a unit and the number of photons of the incident light is calculated based on the summed value.

Effects of the Invention

According to the present technique, accuracy of photon counting can be improved.

BRIEF DESCRIPTION OF DRAWINGS

FIG. 7A to FIG. 7D are views schematically illustrating examples of an exposure operation and a readout operation of the imaging element 110 of the first embodiment of the present technique.

FIG. 9 is a flowchart illustrating an example of a processing procedure in a case where the light detection apparatus 10 of the first embodiment of the present technique performs a photon counting operation.

FIG. 17A to FIG. 17D are views each of which schematically illustrates examples of an exposure operation and a readout operation of each group of the imaging circuits 520 separated into four groups in the fourth embodiment of the present technique.

MODE FOR CARRYING OUT THE INVENTION

The following is a description of modes (hereinafter referred to as embodiments) for carrying out the present technique. Description will be made in the following order.
1. First Embodiment (imaging control: example of performing photon counting by uniformizing incident light by a light uniformizing unit)
2. Second Embodiment (imaging control: example of performing photon counting by masking a pixel having high dark current)
3. Third Embodiment (imaging control: example in which a plurality of pixel array units is provided to one imaging element)
4. Fourth Embodiment (imaging control: example of separating a plurality of pixel array units into groups and performing a different exposure operation on each group)
5. Application Example of Present Technique 1. First Embodiment

[Example of Function Structure of Light Detection Apparatus]

Figure 1:
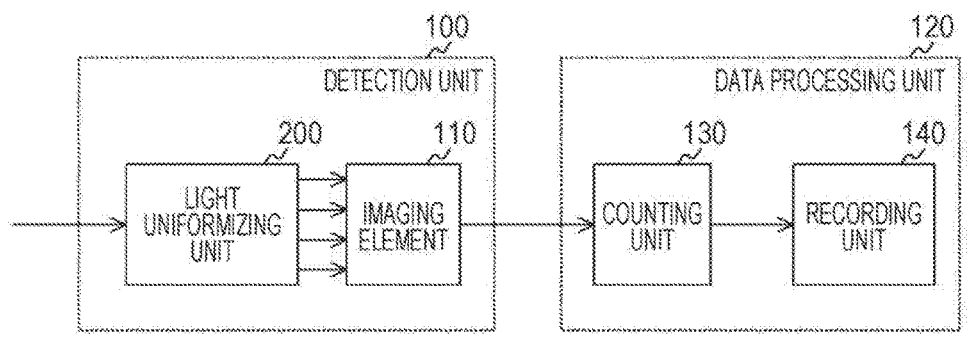
FIG. 1 is a block diagram illustrating an example of function structure related to a light detection apparatus 10 according to a first embodiment of the present technique.

FIG. 1 is a block diagram illustrating an example of function structure related to a light detection apparatus 10 according to a first embodiment of the present technique.

The light detection apparatus 10 is an imaging apparatus to perform photon counting by using a complementary metal oxide semiconductor (CMOS) sensor, and includes a detection unit 100 and a data processing unit 120.

The detection unit 100 converts light incident to the detection unit 100 into a digital signal, and includes a light uniformizing unit 200 and an imaging element 110.

The light uniformizing unit 200 substantially uniformizes distribution of light (light to be object of photon counting) incident to the detection unit 100, and emits, to a pixel array of the imaging element 110, the substantially uniformized light to be an object of photon counting. That is, the light uniformizing unit 200 distributes light, which is to be an object of photon counting and is incident to an entrance plane (orthogonal direction toward optical axis of the imaging element 110) in a non-uniformly distributed manner, in such a manner that the same number of pieces of the light becomes incident to each pixel in the pixel array of the imaging element 110.

The light uniformizing unit 200 is realized, for example, by a kaleidoscope using reflection, an integrated lens such as a fly-eye lens in which small lenses are arranged, a diffraction-optical element (DOE) using diffraction, or a light-scattering material to which a tiny particle or a dot to scatter light on glass or resin is added. Also, the light uniformizing unit 200 can be realized by an optical fiber including a light uniformizing function, or a light guide in which a plurality of optical fibers including the light uniformizing function are bundled. A reason why the light is uniformized by the light uniformizing unit 200 will be described later with reference to FIG. 6, and thus, a description thereof is omitted here.

The imaging element 110 produces an image signal by photoelectric conversion of incident light into an electric signal, and pixels are arranged thereto in an array. The imaging element 110 is realized, for example, by a complementary metal oxide semiconductor (CMOS) sensor. The imaging element 110 will be described later with reference to FIG. 3 to FIG. 5B, and thus, a description thereof is omitted here. In the imaging element 110, it is determined by binary determination whether there is photon incidence into each pixel. The imaging element 110 supplies, to the data processing unit 120, data (digital data) indicating a result of the binary determination.

The data processing unit 120 calculates intensity (count value) of light to be an object of photon counting based on the data (digital data) supplied by the imaging element 110. The data processing unit 120 includes a counting unit 130 and a recording unit 140.

The counting unit 130 calculates intensity (count value) of light to be an object of photon counting in one frame, based on the data supplied by the imaging element 110. For example, the counting unit 130 calculates a count value in one frame by adding values (0 or 1) of digital data of all pixels. The counting unit 130 supplies the calculated count value to the recording unit 140, and the recording unit 140 records the count value. The counting unit 130 is an example of a calculation unit described in claims.

When the counting unit 130 holds positional information (address information) of a pixel having high dark current, mask processing of the pixel having high dark current and correction processing of a count value related to the pixel having high dark current can be performed. Examples of the mask processing of a pixel having high dark current and the correction processing of a count value related to the pixel having high dark current will be described later in the second embodiment of the present technique, and thus, an example not considering dark current will be described in the first embodiment of the present technique.

The recording unit 140 records a count value supplied by the counting unit 130.

Next, as an example of application of the light detection apparatus 10, a schematic view of a detection head of a fluorescence detector will be described with reference to FIG. 2.

[Structure Example of Detection Head]

Figure 2:
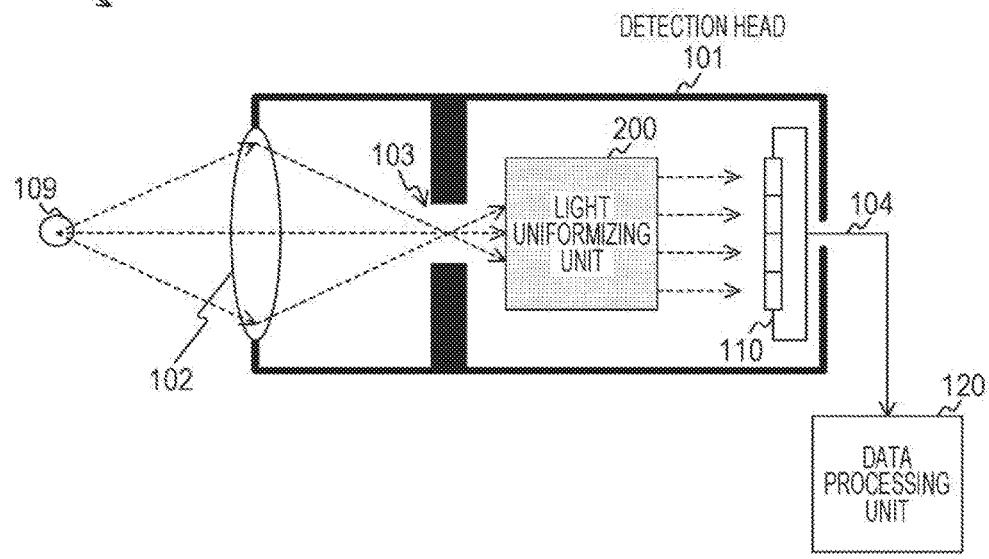
FIG. 2 is a conceptual diagram illustrating an example of a detection head (detection head 101) to which the light detection apparatus 10 according to the first embodiment of the present technique is applied.

FIG. 2 is a conceptual diagram illustrating an example of a detection head (detection head 101) to which the light detection apparatus 10 according to the first embodiment of the present technique is applied.

The detection head 101 receives light (here, fluorescence is assumed in description) emitted by a spot to be detected (detection spot 109) and measures intensity of the light. The detection head 101 includes a condensing lens 102, a pinhole 103, the light uniformizing unit 200, and the imaging element 110. In FIG. 2, the digital data output by the imaging element 110 is supplied to the data processing unit 120 through a signal wire 104. The light uniformizing unit 200, the imaging element 110, and the data processing unit 120, which are illustrated in FIG. 2, have been described in FIG. 1, and thus, the description thereof is omitted here.

For convenience of description, a structure related to excitation light of fluorescence is not illustrated and a description will be made focusing on the detection head 101. Also, a band-pass filter or a cut-off filter is arranged in an optical path in such a manner that the excitation light is blocked and only the fluorescence passes through the pinhole 103, but a description thereof is also omitted.

The condensing lens 102 condenses pieces of light. The light incident to an entrance plane of the condensing lens 102, among pieces of fluorescence emitted by the detection spot 109, are collected to the pinhole (pinhole 103).

The pinhole 103 is a hole provided at a position where the fluorescence, which is emitted by the spot to be detected and passes through the condensing lens 102, is condensed again. Fluorescence generated outside a focusing position (spot to be detected) is not condensed to the pinhole 103, whereby most of the fluorescence generated outside the focusing position is blocked by a blocking member which forms the pinhole 103. Thus, incidence, to the light uniformizing unit 200, of the fluorescence generated outside the focusing position is prevented. That is, the pinhole 103 decreases the incidence, to the light uniformizing unit 200, of the fluorescence generated outside the focusing position (outside detection spot 109) and decreases background noise.

As illustrated in FIG. 2, in the detection head 101, the fluorescence having passed through the pinhole 103 becomes incident to the light uniformizing unit 200, and the light uniformized by the light uniformizing unit 200 becomes incident to the imaging element 110. In the conventional detection head, the fluorescence having passed through the pinhole 103 is detected by a photomultiplier tube (PMT) (see FIG. 8A). However, in the embodiments of the present technique, instead of the photomultiplier tube, the light uniformizing unit 200 and the imaging element 110 are provided.

For example, in a fluorescence scanner, the detection head 101 illustrated in FIG. 2 and an excitation light source are moved in steps relatively to an object, and thus, fluorescence intensity distribution of a wide inspection region can be detected.

Next, a structure example of the imaging element 110 will be described with reference to FIG. 3 to FIG. 5B.

[Example Structure of Imaging Element]

Figure 3:
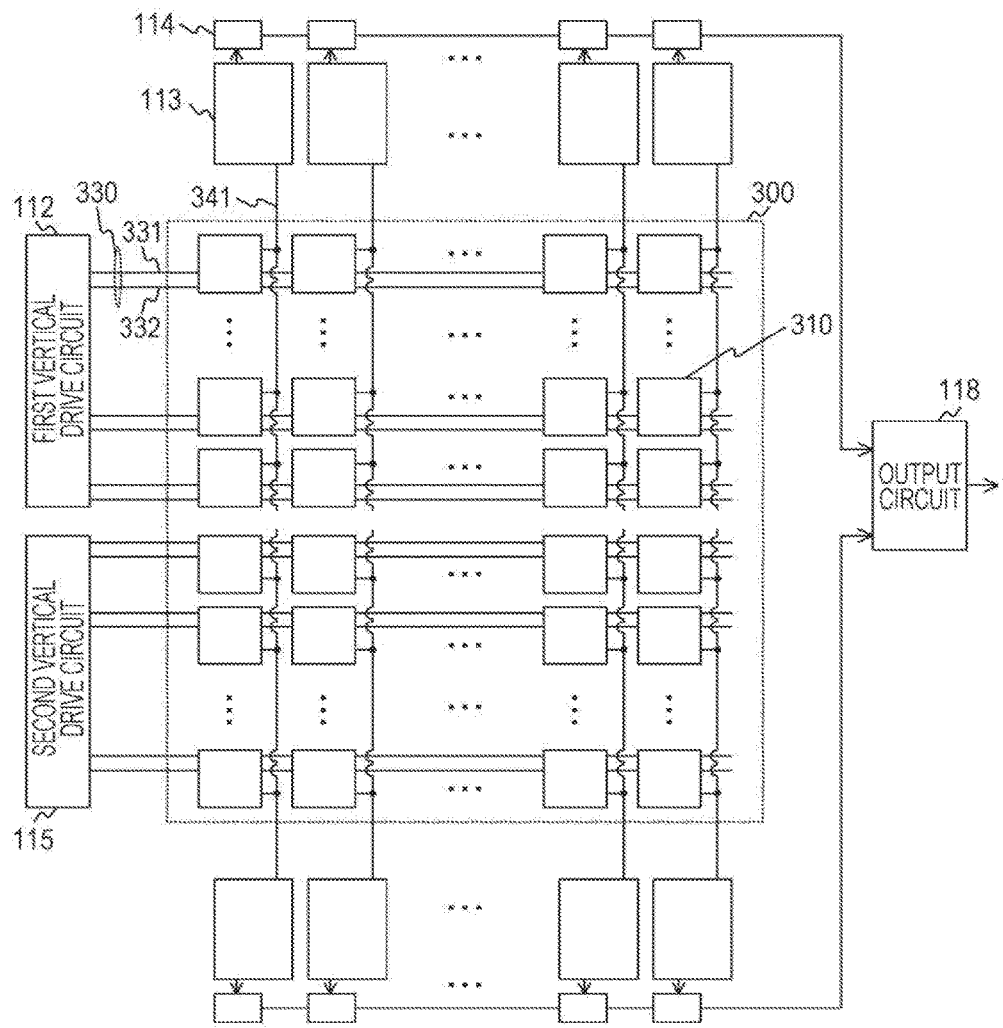
FIG. 3 is a conceptual diagram illustrating an example of a basic structure of an imaging element 110 of the first embodiment of the present technique.

FIG. 3 is a conceptual diagram illustrating an example of a basic structure of the imaging element 110 of the first embodiment of the present technique.

In the description of FIG. 3, it is assumed to drive (control) with two vertical control circuits to increase the speed of readout.

The imaging element 110 includes a pixel array unit 300, a first vertical drive circuit 112, a determination circuit 113, a register 114, a second vertical drive circuit 115, and an output circuit 118. A determination circuit and a register, which are driven by the second vertical drive circuit 115, to process a signal of a pixel are similar to a determination circuit (determination circuit 113) and a register (register 114), which are driven by the first vertical drive circuit 112, to process a signal of a pixel. Thus, a description of the determination circuit and the register driven by the second vertical drive circuit 115 is omitted.

The pixel array unit 300 includes a plurality of pixels (pixel 310) arranged in a two-dimensional matrix (n×m). In the first embodiment of the present technique, it is assumed that the 128 lines×128 rows of the pixels 310 are arranged in the pixel array unit 300. In the pixel array unit 300 illustrated in FIG. 3, a part of 128 lines×128 rows of the pixels 310 is illustrated. To a half of the pixels 310 arranged in the pixel array unit 300 (pixel placed in upper half of pixel array unit 300 in FIG. 3), a control wire (control wire 330) is arranged in a line unit from the first vertical drive circuit 112. On the other hand, to the remaining half of the pixels (pixel placed in lower half of the pixel array unit 300 in FIG.

3), a control wire is arranged in a line unit from the second vertical drive circuit 115. A circuit structure of the pixel 310 will be described later with reference to FIG. 4, and thus, a description thereof is omitted here.

Also, to the pixel 310, a vertical signal wire (vertical signal wire 341) is arranged in a row unit. Different vertical signal wires 341 are respectively arranged according to vertical drive circuits to which the pixels 310 are connected. The vertical signal wire 341 connected to a pixel, to which the control wire 330 is arranged from the first vertical drive circuit 112, is connected to the determination circuit 113 which faces an upper side of the pixel array unit 300. Also, the vertical signal wire 341 connected to a pixel, to which a control wire 330 is arranged from the second vertical drive circuit 115, is connected to the determination circuit 113 which faces a lower side of the pixel array unit 300.

The first vertical drive circuit 112 supplies a signal to the pixels 310 through the control wire 330, and selectively scans the pixels 310 in a line unit serially in a vertical direction (direction of row). The first vertical drive circuit 112 performs the selective scan in a line unit, and thus, the pixels 310 output a signal in a line unit. The control wire 330 includes a pixel reset wire 331 and a charge transfer wire 332. The pixel reset wire 331 and the charge transfer wire 332 will be described later with reference to FIG. 4, and thus, a description thereof is omitted here.

Also, the second vertical drive circuit 115 is similar to the first vertical drive circuit 112 except that the pixels 310 to be controlled thereby are different from those to be controlled by the first vertical drive circuit 112. Thus, a description of the second vertical drive circuit 115 is omitted here. Since the pixels 310 are driven by the first vertical drive circuit 112 and the second vertical drive circuit 115, two lines are selectively scanned substantially at the same time, and readout from the two lines is performed substantially at the same time.

The determination circuit 113 determines (binary determination) whether there is incidence of photons to the pixels 310, based on the output signal supplied by the pixels 310. The determination circuit 113 is included by each of the vertical signal wires 341. That is, in the place facing the upper side of the pixel array unit 300, 128 determination circuits 113, which are respectively connected to 128 vertical signal wires 341 arranged to the pixels (64 lines×128 rows) driven by the first vertical drive circuit 112, are included. Also, in the place facing the lower side of the pixel array unit 300, 128 determination circuits 113, which are respectively connected to 128 vertical signal wires 341 arranged to the pixels (64 lines×128 rows) driven by the second vertical drive circuit 115, are included.

The determination circuit 113 supplies a determination result to the register 114 connected to each determination circuit 113.

The register 114 is included by each determination circuit 113, and temporally holds the determination result supplied by the determination circuit 113. The register 114 serially outputs the holding determination result to the output circuit 118 during a period in which a signal of a next line of the pixels is being read (readout period).

The output circuit 118 outputs the signal generated by the imaging element 110 to an external circuit.

Next, an example of a circuit structure of the pixel 310 will be described with reference to FIG. 4.

[Circuit Structure Example of Pixel]

Figure 4:
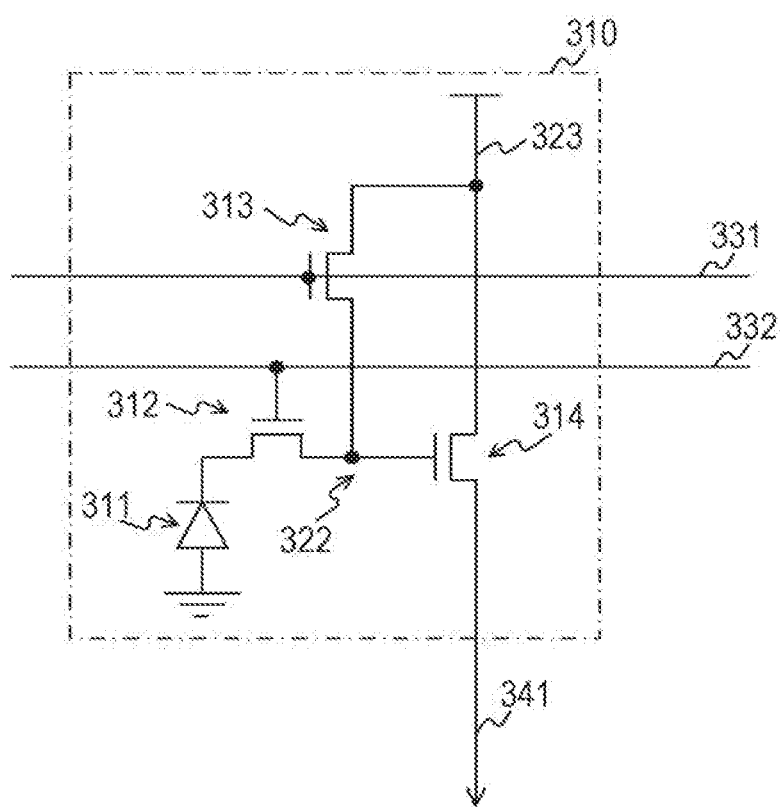
FIG. 4 is a schematic view illustrating an example of a circuit structure of a pixel 310 of the first embodiment of the present technique.

FIG. 4 is a schematic view illustrating an example of a circuit structure of a pixel 310 of the first embodiment of the present technique.

The pixel 310 converts an optical signal, which is incident light, into an electric signal by photoelectric conversion. The pixel 310 amplifies the converted electric signal and outputs the signal as a pixel signal. The pixel 310 amplifies the electric signal, for example, by a floating-diffusion amplifier including an FD layer.

The pixel 310 includes a photodiode 311, a transfer transistor 312, a reset transistor 313, and an amplifier transistor 314.

In the pixel 310, an anode terminal of the photodiode 311 is grounded and a cathode terminal thereof is connected to a source terminal of the transfer transistor 312. Also, a gate terminal of the transfer transistor 312 is connected to the charge transfer wire 332, and a drain terminal thereof is connected to a source terminal of the reset transistor 313 and a gate terminal of the amplifier transistor 314 through floating-diffusion (FD 322).

Also, a gate terminal of the reset transistor 313 is connected to the pixel reset wire 331, and a drain terminal thereof is connected to a power wire 323 and a drain terminal of the amplifier transistor 314. Also, a source terminal of the amplifier transistor 314 is connected to the vertical signal wire 341.

The photodiode 311 is a photoelectric conversion element to generate charge according to intensity of light. In the photodiode 311, a pair of an electron and a hole is generated by the photon incident to the photodiode 311, and the generated electron is accumulated.

The transfer transistor 312 transfers, to the FD 322, the electron generated in the photodiode 311, according to a signal (pulse) from a vertical drive circuit (first vertical drive circuit 112 or second vertical drive circuit 115). For example, the transfer transistor 312 becomes conductive when a signal (pulse) for the gate terminal thereof is supplied by the charge transfer wire 332 to the gate terminal. Then, the transfer transistor 312 transfers, to the FD 322, the electron generated in the photodiode 311.

The reset transistor 313 resets an electric potential of the FD 322, according to a signal (reset pulse) supplied by the vertical drive circuit (first vertical drive circuit 112 or second vertical drive circuit 115). The reset transistor 313 becomes conductive when the reset pulse is supplied to the gate terminal thereof through the pixel reset wire 331, and electric current flows from the FD 322 to the power wire 323. Thus, the electron accumulated in the floating-diffusion (FD 322) is extracted to a power source, and the floating-diffusion is reset (hereinafter electric potential at this time will be referred to as reset electric potential). When the photodiode 311 is reset, the transfer transistor 312 and the reset transistor 313 become conductive at the same time. Thus, the electron accumulated in the photodiode 311 is extracted to the power source, and a reset to a state (dark state), in which there is no incidence of a photon, is performed. The electric potential (power source), which flows in the power wire 323, is a power source used for a reset or a source follower, and supplies, for example, 3V.

The amplifier transistor 314 amplifies an electric potential of the floating-diffusion (FD 322) and outputs, to the vertical signal wire 341, a signal (output signal) corresponding to the amplified electric potential. When the electric potential of the floating-diffusion (FD 322) is in a reset state (in case of reset electric potential), the amplifier transistor 314 outputs, to the vertical signal wire 341, an output signal corresponding to the reset electric potential (hereinafter referred to as reset signal). Also, when the electron accumulated in the photodiode 311 is transferred to the FD 322, the amplifier transistor 314 outputs, to the vertical signal wire 341, an output signal corresponding to a quantity of transferred electrons (hereinafter referred to as accumulated signal).

A basic circuit or an operation mechanism of the pixel illustrated in FIG. 4 is similar to that of a normal pixel, and there may be many other variations. However, the pixel assumed in the present technique is designed to have much higher conversion efficiency than the conventional pixel. For the high conversion efficiency, the pixel is designed in such a manner that parasitic capacity of a gate terminal of an amplifier (amplifier transistor 314) forming a source follower (parasitic capacity of FD 322) is effectively minimized. This design can be made, for example, by a method to enhance layout or a method to feedback output of a source follower to a circuit in a pixel (see, for example, JP 5-63468 A and JP 2011-119441 A).

In this manner, the parasitic capacity is minimized, and thus, a sufficiently large output signal is output to the vertical signal wire 341, even when a small quantity of electrons are accumulated in the FD 322. The size of the output signal only needs to be sufficiently larger than that of random noise of the amplifier transistor 314. When an output signal, in a case where one photon is accumulated in the FD 322, is sufficiently larger than the random noise of the amplifier transistor 314, a signal from the pixel is quantized and it becomes possible to detect the number of accumulated photons in the pixel as a digital signal.

For example, when the random noise of the amplifier transistor 314 is around 50 μV to 100 μV and in a case where the conversion efficiency of the output signal is raised to around 600 μV/e$^-$, the output signal is sufficiently larger than the random noise. Thus, one photon can be detected, in principle.

Note that, when binary determination is performed to determine whether there is photon incidence during a unit exposure period and a result thereof is digitally output, noise after the output of the output signal by the amplifier transistor 314 can be substantially zero. For example, when binary determination is performed in respect to a 128 lines×128 rows pixel array, photon counting can be performed on up to 16,384 (128×128) photons.

In FIG. 4, an example of a pixel, in which the pixel is designed in such a manner that the parasitic capacity is minimized effectively and one photon can be detected, has been described, but a pixel is not limited thereto. Alternatively, a pixel, in which an electron obtained by photoelectric conversion is amplified therein, can also be used in the embodiment. For example, a pixel, in which a plurality of stages of CCD multiplication transfer elements are embedded between a photodiode in the pixel and a gate terminal of an amplifier transistor, may be considered (see, for example, JP 2008-35015 A). In the pixel, an electron photoelectrically converted is amplified by about 10 times therein. In this manner, by amplifying the electron in the pixel, it is also possible to detect one photon, and an imaging element to which such a pixel is arranged can also be used as the imaging element 110.

Next, the determination circuit 113, which determines whether there is incidence of photon into the pixel 310 based on an output signal supplied by the pixel 310, will be described with reference to FIG. 5A and FIG. 5B.

[Structure Example of Determination Circuit 113]

Figures 5A, 5B:
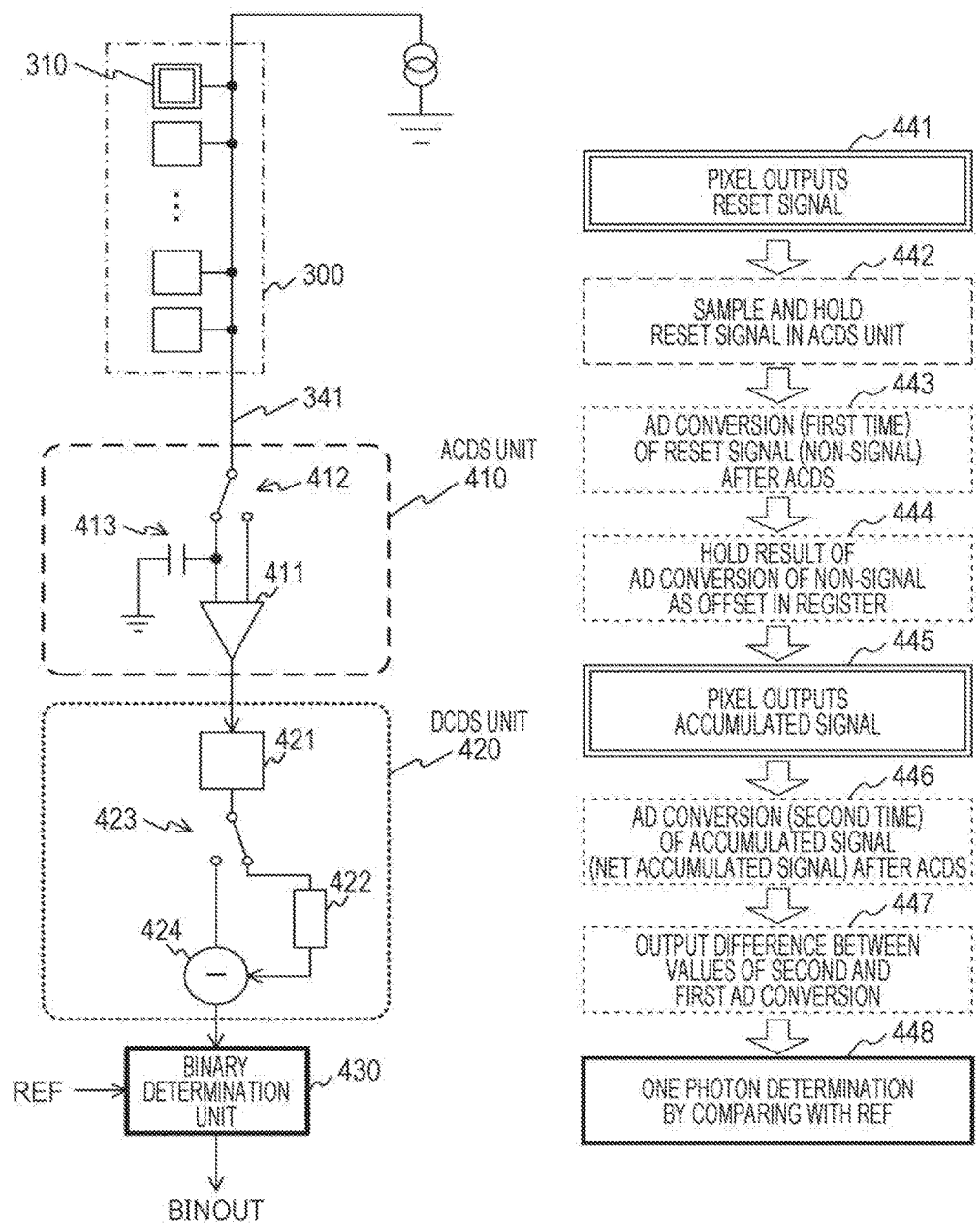
FIG. 5A and FIG. 5B are conceptual diagrams illustrating an example of a function structure and an operation example of a determination circuit 113 of the first embodiment of the present technique, respectively.

FIG. 5A and FIG. 5B are conceptual diagrams illustrating an example of a function structure and an operation example of the determination circuit 113 of the first embodiment of the present technique.

In FIG. 5A, as a function structure of the determination circuit 113, an analog correlated double sampling (ACDS) unit 410, a digital CDS (DCDS) unit 420, and a binary determination unit 430 are illustrated.

Also, in FIG. 5A, the vertical signal wire 341 connected to the determination circuit 113, a part of the pixel 310 connected to the vertical signal wire 341, and the pixel array unit 300 are illustrated with the function structure of the determination circuit 113.

The ACDS unit 410 removes noise by analog CDS, and includes a switch 412, a capacitor 413, and a comparator 411.

The switch 412 connects the vertical signal wire 341 to either an input terminal which inputs reference voltage into the comparator 411 or an input terminal which inputs a signal to be compared into the comparator 411. When a reset signal of the pixel 310 is sampled and held, the switch 412 connects the vertical signal wire 341 to the input terminal (left side terminal to which capacitor 413 is connected) which inputs reference voltage. Also, when the comparator 411 outputs a result of the analog CDS, the switch 412 connects the vertical signal wire 341 to the input terminal (right side terminal without capacitor) which inputs a signal to be compared.

The capacitor 413 is a holding capacitor to sample and hold the reset signal of the pixel 310.

The comparator 411 outputs difference between the signal sampled and held and the signal to be compared. That is, the comparator 411 outputs the difference between the reset signal sampled and held and the signal (accumulated signal or reset signal) supplied by the vertical signal wire 341. That is, the comparator 411 outputs a signal in which noise, such as kTC noise, generated in the pixel 310 is removed. The comparator 411 is realized, for example, by an operational amplifier of a gain 1. The comparator 411 supplies a differential signal to the DCDS unit 420. Note that here, a differential signal between a reset signal and a reset signal is referred to as a non-signal, and a differential signal between a reset signal and an accumulated signal is referred to as a net accumulated signal.

The DCDS unit 420 removes noise by digital CDS, and includes an analog digital (AD) conversion unit 421, a register 422, a switch 423, and a subtracter 424.

The AD conversion unit 421 performs AD conversion on a signal supplied by the comparator 411.

The switch 423 switches supply destinations of a signal, which is a signal after the AD conversion, generated by the AD conversion unit 421. When the AD conversion unit 421 outputs a result of the AD conversion of a non-signal (digital non-signal), the switch 423 supplies the signal to the register 422 and the register 422 latches (hold) the signal. Thus, an offset value of the AD conversion unit 421 is held in the register 422. Also, when the AD conversion unit 421 outputs a result of the AD conversion of a net accumulated signal (digital net accumulated signal), the switch 423 supplies the signal to the subtracter 424.

The register 422 holds a result of the AD conversion of a non-signal. The register 422 supplies, to the subtracter 424, the holding result of the AD conversion of a non-signal (digital non-signal).

The subtracter 424 subtracts a value of the digital non-signal from a value of the net digital accumulated signal. The subtracter 424 supplies a result of the subtraction (net digital value) to the binary determination unit 430.

The binary determination unit 430 performs binary determination (digital determination). The binary determination unit 430 compares output of the subtracter 424 (net digital value) and a reference signal (REF), and performs binary determination to determine whether there is incidence of a photon to the pixel 310. Then the binary determination unit 430 outputs a determination result (in FIG. 5A, referred to as "BINOUT").

Here, operation of the determination circuit 113 in a case of performing binary determination to determine whether there is incidence of a photon to one pixel 310 will be described with reference to FIG. 5B.

FIG. 5B is a flowchart illustrating an operation example of the determination circuit 113. A frame of each step in the flowchart illustrated in FIG. 5B corresponds to a frame surrounding each structure illustrated in FIG. 5A. That is, a step surrounded by a double frame indicates a step of the pixel 310, a step surrounded by a long-dashed frame indicates a step of the ACDS unit 410, a step surrounded by a short-dashed frame indicates a step of the DCDS unit 420, and a step surrounded by a heavy solid frame indicates a step of the binary determination unit 430. Note that for convenience of description, ACDS processing by the ACDS unit 410 is not illustrated and will be described together in a description of a step in which the DCDS unit 420 performs AD conversion.

First, in a pixel (pixel 310) of a selected line, an electric potential of a gate terminal of the amplifier transistor 314 (electric potential of the FD 322) is reset, and a reset signal is output to the vertical signal wire 341 (step 441).

Next, the reset signal output from the pixel 310 is sampled and held by the capacitor 413 of the ACDS unit 410 (step 442). Then, AD conversion is performed, by the AD conversion unit 421 of the DCDS unit 420, on a differential signal (non-signal) between the reset signal sampled and held and the reset signal output from the pixel 310 (step 443). In the non-signal on which the AD conversion is performed, noise generated by the comparator 411 or the AD conversion unit 421 is included, and a value to cancel (offset) the noise is digitally detected. Then, the result of the AD conversion of the non-signal is held, as an offset value, in the register 422 (step 444).

Next, in the pixel 310, the electron accumulated in the photodiode 311 is transferred to the FD 322, and an accumulated signal is output from the pixel 310 (step 445). Then, AD conversion is performed, by the AD conversion unit 421 of the DCDS unit 420, on a differential signal (net accumulated signal) between the reset signal sampled and held and the accumulated signal output from the pixel 310 (step 446). In the result of the AD conversion, noise generated by the comparator 411 or the AD conversion unit 421 is included.

Then, a value, in which a value of the result of the AD conversion (first time) of the non-signal held in the register 422 is subtracted from a value of the result of the AD conversion (second time) of the net accumulated signal, is output by the subtracter 424 (step 447). Thus, the noise (offset component) caused by the comparator 411 or the AD conversion unit 421 is canceled, and a digital value (net digital value) only including the accumulated signal output by the pixel 310 is output.

Then, the net digital value output from the subtracter 424 and a reference signal (REF) are compared by the binary determination unit 430 (step 448). As the reference signal (REF), a value around an intermediate value of a digital value of a signal (non-signal), which is output by the pixel 310 in a case where there is no photon incidence, and a digital value of a signal (non-signal), which is output by the pixel 310 in a case where there is photon incidence, is set (for example, "50" which is an intermediate of "0" and "100" is reference signal). When the digital value output by the subtracter 424 (digital value only including the accumulated signal output by pixel 310) is over the value of the reference signal (REF), a signal (BINOUT) of the value "1" is output to indicate "there is photon incidence". On the other hand, the digital value output by the subtracter 424 is not over the value of the reference signal (REF), a signal (BINOUT) of the value "0" is output to indicate "there is no photon incidence". That is, from the imaging element 110, existence or non-existence of photon incidence is output as a digital value (0 or 1) of a result of the binary determination.

In FIG. 5A and FIG. 5B, the description has been made on the assumption that binary determination to determine whether "there is photon incidence" or "there is no photon incidence" is performed. However, by preparing reference signals (REF) of a plurality of systems, determination more than binary becomes possible. For example, reference signals (REF) of two systems are prepared and an intermediate value of a digital value in a case where the number of photons is "0" and a digital value in a case where the number of photons is "1" is set to one system. Also, an intermediate value of a digital value in a case where the number of photons is "1" and a digital value in a case where the number of photons is "2" is set to the remaining one system. Thus, it becomes possible to perform determination in three cases where the number of photons is "0", "1", and "2", and a dynamic range of the imagining is improved. In such multi-value determination, an impact, caused by variation in conversion efficiency of pixels or the like, becomes large, and thus, a production thereof needs to be performed with higher accuracy than a production of binary determination. However, the multi-value determination is similar to the binary determination, which only determines whether there is photon incidence or not (0 or 1) based on a signal generated by a pixel, in a point that a signal generated by a pixel is treated as digital output.

In this manner, in the imaging element 110, the signal output by the pixel 310 is determined as a digital value in the determination circuit 113. Thus, there is almost no impact caused by noise during transmission, compared to the conventional imaging element (1024 gradations in case of 10 bit data) which treats the signal as analog output.

Next, a relationship between the number of photons incident to each pixel and a detection result will be described with reference to FIG. 6.

[Relationship Example Between the Number of Photons Incident to Each Pixel and Detected Result]

Figure 6:
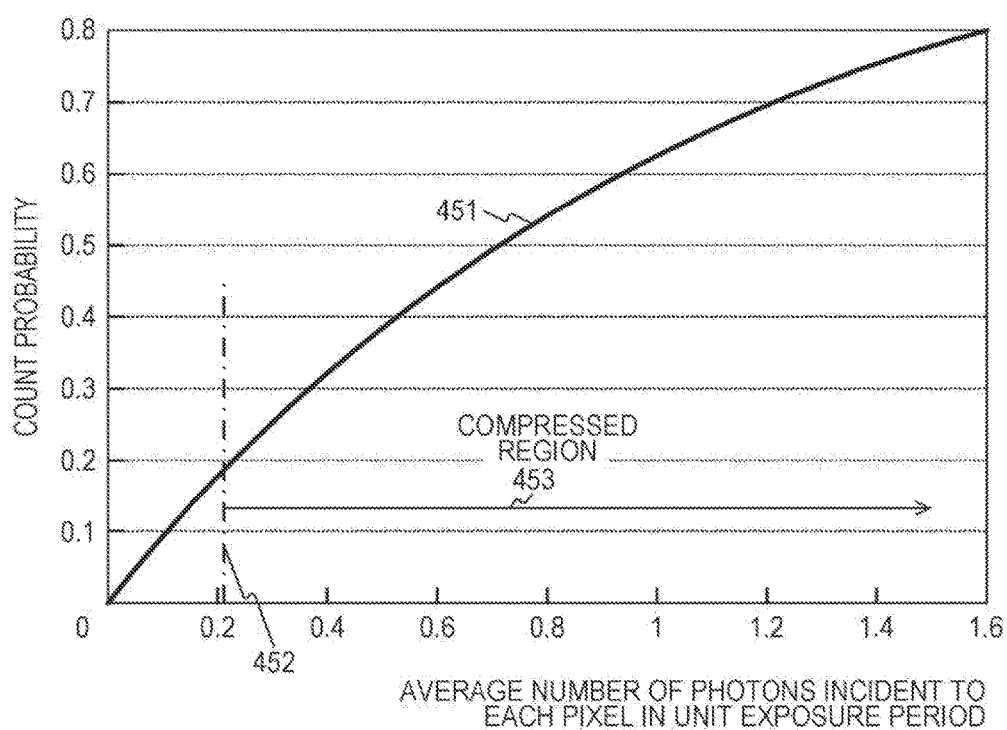
FIG. 6 is a chart illustrating a relationship between the average number of photons incident to each pixel in a unit exposure period and a count probability, according to the first embodiment of the present technique.

FIG. 6 is a chart illustrating a relationship between the average number of photons incident to each pixel in a unit exposure period and a count probability, according to the first embodiment of the present technique.

Photons are incident to each pixel of the imaging element 110 uniformly and randomly by the light uniformizing unit 200. It is assumed that the photons are incident also in a temporally uniform and random manner.

In such a condition, a relationship between the average number of photons incident to each pixel in a unit exposure period (average number of photons) and provability (count probability) of the incident photon being counted (determined as "1" in the determination circuit 113) follows Poisson distribution. Since the relationship between the average number of photons and the count probability follows the Poisson distribution, the relationship can be expressed in the following formula 1.

[Mathematical Formula 1]

Here, P(k) is provability of photon incidence to a unit pixel happening k times (number of incident photons is k) in a unit exposure period. Also, λ is the average number of photons (average number of photons) which become incident to the unit pixel in the unit exposure period. Also, e is the base of natural logarithms (≈2.718).

That is, the provability P(k) of the formula 1 expresses provability of the number of incident photons being k in a case where the number of photons which become incident to each pixel in the unit exposure period is the average number of photons λ.

Here, the relationship between the average number of photons and the count probability will be described on the assumption that the average of the number of photons (average number of photons λ) incident to each pixel of the imaging element 110 in the unit exposure period is "0.21". In this case, a relationship between the number of photons k and the provability P(k) is as follows, based on the formula 1.

Provability of the number of photons incident to a unit pixel being 0 (k=0): 0.8105

Provability of the number of photons incident to a unit pixel being 1 (k=1): 0.1702

Provability of the number of photons incident to a unit pixel being 2 (k=2): 0.0179

Provability of the number of photons incident to a unit pixel being 3 (k=3): 0.0013

. . . (the rest is omitted since values thereof are very small (0.00007 or less.))

Next, a signal generated by the imaging element 110 in a case where the photon becomes incident in such provability.

The determination circuit 113 of the imaging element 110 performs binary determination to determine whether there is photon incidence to a pixel. A case where a digital value output by the determination circuit 113 is "0" is the case where the number of photons incident to the unit pixel is zero. That is, provability of the digital value being "0" is "0.8105" which is the provability of the case where the number of photons incident to the unit pixel is zero.

On the other hand, a case where a digital value output by the determination circuit 113 is "1" is all of the cases where the number of photons incident to the unit pixel is one or more. That is, provability (count probability) of the digital value being "1" is "0.1894" which is a value in which the provability of the cases, where one or more photons are incident to the unit pixel, is summed.

Since the average number of photons λ is "0.21", the count probability "0.1894" indicates that about 10% of the incident photons are not counted (count loss). The count loss is caused by counting incidence of two or more photons to the unit pixel in the unit exposure period is counted as "1". Thus, the greater the average number of photons λ is, the greater the count loss becomes.

In the above, a description has been made on the assumption that the average number of photons λ is "0.21". Such a relationship between the average number of photons λ and the count probability is unique in a case where the photons are incident in a spatially and temporally uniform and random manner. That is, when a vertical axis indicates count probability and a horizontal axis indicates the average number of photons incident to each pixel in the unit exposure period, a relationship between the count probability and the average number of photons is indicated by a solid line (line 451) in the chart of FIG. 6.

In the chart of FIG. 6, a position of the average number of photons indicated by a dot-dash line (dot-dash line 452) indicates a position where a count loss of about 10% of the incident photons is caused (position of 10% detection loss). In the embodiments of the present technique, the count loss of about 10% is allowed, and description is made on the assumption that the linearity can be secured when the average number of photons is "0.21" or less. When viewed from the side of a digital output value generated by the imaging element 110, that is, in a case where the count probability in the digital value generated by the imaging element 110 is "0.1894" or less, it is determined that imaging is performed with illuminance and an exposure condition which can secure the linearity. On the other hand, when the count probability is over "0.1894" (in a range indicated in a compressed region 453 of FIG. 6), there are too much count loss and it is determined that the linearity cannot be secured.

Between the count probability and the average number of photons, there is such a relationship indicated in the chart of FIG. 6. Thus, by making it hold the data (such as Poisson distribution, or function or table approximate to Poisson distribution) indicating a relationship similar to that indicated in the chart, a count value can be corrected. In this correction, first, count probability (percentage of pixel having value "1" in all pixel) is calculated based on a digital value generated by the imaging element 110. Then, the average number of photons is calculated from the count probability and the data indicating the relationship illustrated in the chart of FIG. 6. Then, the number of photons incident to the imaging element 110 is calculated from the calculated average number of photons. When this correction is performed, compared to a case of using in a range in which the linearity can be secured (in a case of no correction), a detection dynamic range can be raised by about one digit.

Next, an exposure operation and a readout operation of the imaging element 110 will be described with reference to FIG. 7A to FIG. 7D, on the assumption that fluorescence detection is performed with the light detection apparatus 10 being mounted to a fluorescence scanner for an imaging plate of an X-ray.

Here, the imaging plate stores a latent image of the X-ray transmitted through a human body. When excitation light is emitted by the fluorescence scanner, this imaging plate generates light (photostimulated luminescence) according to the latent image of the X-ray. The fluorescence scanner obtains an X-ray picture of a wide dynamic range, without using a film or darkroom development, by detecting the generated photostimulated luminescence.

[Example of Exposure Operation and Readout Operation of Imaging Element 110]

FIG. 7A and FIG. 7B are views schematically illustrating examples of an exposure operation and a readout operation of the imaging element 110 of the first embodiment of the present technique.

In FIG. 7A and FIG. 7B, a description is made on the assumption of a case where readout is performed serially from the first line right after the excitation light is emitted to the imaging plate of the X-ray. Also, in FIG. 7C and FIG. 7D, a description is made on the assumption of a case where the excitation light is emitted while the readout is serially being performed (during readout of halfway line).

In FIG. 7A, readout timing of a signal of the imaging element 110 (readout timings 462 to 464) is schematically illustrated with a horizontal direction indicating a time axis and a vertical direction indicating a line (readout line address) from which a signal is read. Also, in FIG. 7A, a period from a start to an end of the exposure (unit exposure period 466) and emission timing of the excitation light (excitation light emission timing 467) are illustrated.

Readout timing, at which the light generated by excitation at the excitation light emission timing 467 is detected, is indicated by a heavy diagonal line among diagonal lines indicating the readout timings 462 to 464. In the FIG. 7A, the readout timing, at which the light generated by the excitation is detected, corresponds to the readout timing 463. That is, all of the accumulated signals, which are generated by the pixel from the light generated by the excitation, is read during a period from the readout of the first line (left end of the readout timing 463) to the readout of the last line (right end of the readout timing 463) in the readout timing 463.

Here, readout operation of the light detection apparatus 10 in a case where readout is serially performed from the first line right after the excitation light is emitted to the imaging plate will be described.

When the readout is serially performed from the first line right after the excitation light is emitted to the imaging plate, a position of an object to be detected (detection spot) is moved to a position right after a previous readout is completed (to right end of the readout timing 462). Then, an excitation light pulse is emitted to the moved detection spot (excitation light emission timing 467). Due to the emission of the excitation light, photostimulated luminescence is generated corresponding to absorption amount (latent image) of X-ray at the detection spot. Generation of the light (fluorescence) by the photostimulated luminescence is attenuated in about 1 μs. 1 μs is shorter than a readout period of one line of the imaging element 110. For example, in a case where time of a round of readout (time from left end to right end of the readout timing 463) is 320 μs, 1 μs is quite short, and thus, it means that great number of photons are generated substantially at the same time.

Among the generated photons, photons incident to a condensing lens 102 are emitted, by the light uniformizing unit 200, to the pixel array unit 300 of the imaging element 110 in a substantially uniform and random manner. Thus, the photons are separately received by 128 lines×128 rows of the pixels 310, and electrons are accumulated therein. Then, when readout timing (readout timing 463) starts, accumulated signals corresponding to the accumulated electrons are read serially line by line.

In FIG. 7B, the number of counts of each of the read lines is schematically illustrated, with a horizontal direction being the same time axis in FIG. 7A and a vertical axis being an axis to indicate the number of times of counting (number of count) the digital value "1". It is not possible to illustrate all of 64 lines (128 lines/2), and thus, the number of illustrated lines (number of bars) is schematic.

In a case where readout is performed serially from the first line right after the excitation light is emitted, the accumulated signals, which correspond to the electrons accumulated at the readout timing 463 of FIG. 7A, are serially read. Thus, in FIG. 7B, a plurality of bars indicating the different number of counts are illustrated in a period corresponding to the readout timing 463 of FIG. 7A (readout period of count by photostimulated light 469).

Although omitted in FIG. 7B, by being read 64 times at the readout timing 463 (128 lines are read by two systems), a round of readout of all lines is completed and all incident photons are read to the pixel array unit 300 of the imaging element 110.

In FIG. 7C and FIG. 7D, a case where the excitation light is emitted while the readout is serially performed line by line in the imaging element 110 (during readout of halfway line) is illustrated.

Similarly to FIG. 7A, in FIG. 7C, readout timing of a signal of the imaging element 110 (readout timings 472 to 475) is schematically illustrated. Also, similarly to FIG. 7B, in FIG. 7D, the number of counts of each of the read lines is schematically illustrated. A unit exposure period 476 and an excitation light emission timing 477 of FIG. 7C respectively correspond to the unit exposure period 466 and the excitation light emission timing 467 of FIG. 7A. Also, a readout period of count by photostimulated light 479 of FIG. 7D corresponds to the readout period of count by photostimulated light 469 of FIG. 7B.

As illustrated in FIG. 7C, in a case where excitation light is emitted at timing in the middle of the readout (excitation light emission timing 477), count by the photostimulated light is read from a line to be read after the emission (left end of heavy lined section of the readout timing 473). Then, in a next readout cycle (readout timing 474), count values of lines, from which count by the photostimulated light is not yet read, are read (right end of heavy lined section of the readout timing 474). In the rest (beyond right end of heavy lined section of the readout timing 474), ideally, no count value is read by the photostimulated light.

In this manner, in a case where the excitation light is emitted at the timing in the middle of the readout, data is read in two cycles of the readout timing.

The unit exposure period illustrated in FIG. 7A and FIG. 7B can be shortened by resetting a photodiode at timing different from the readout timing. Also, the unit exposure period can be extended by providing a blank period, in which nothing is performed, between the readout timing of the previous cycle and that of the current cycle. Incidentally, the unit exposure period (unit exposure period 476) of FIG. 7C illustrates an exposure period (normal exposure period) which is not shortened or extended. The unit exposure period (unit exposure period 466) of FIG. 7A illustrates an extended exposure period. Adjustment of the unit exposure period functions as a diaphragm to adjust the amount of incident light in respect to light emission which is kept temporally in a substantially uniform manner.

Here, readout operation from the imaging element 110 will be described by means of numerical values. In the imaging element 110, readout of each line is performed serially in a cycle. As illustrated in FIG. 3, since readout of two lines (two system) is performed at the same time, a round of readout of 128 lines is 64 times (cycle) of readout. When accumulated charge is transferred for the readout, a photodiode is reset. Thus, a period between readout and readout is an exposure period. The exposure period is also an accumulation period of charge which is photoelectrically converted.

For example, in a case where 5 μs are spent to perform a readout step of one line, a basic unit of the exposure period of each pixel is 320 μs (5 μs×64 cycle) in which a round of readout is completed. In this case, 3125 cycles (1 second/320 μs (0.00032 seconds)) of readout is performed in one second.

Here, for example, in normal light detection in which photons are incident temporally in a random manner, up to $51.2 \times 10^6$ (128×128×3125) photons can be counted in one second when one photon become incident to each pixel and is counted.

In this case, as illustrated in FIG. 6, when about 10% of count loss is allowed, linearity can be secured, without correction using Poisson distribution, in respect to a count within a range in which count probability is not over "0.1894". That is, the upper limit, with which the linearity can be secured, of the number of incident photons to the pixel array unit is $9.7 \times 10^6$/second ($51.2 \times 10^6$/second×0.21).

On the other hand, in respect to detection of photostimulated luminescence in the imaging plate, since a photon to be detected becomes incident instantly, a temporal element is ignored and only uniformity and randomness on a plane are secured. In this case, when indicated by the number of counts in a period in which a round of readout from pixels is completed (a period corresponding to readout of one frame), the upper limit, with which the linearity can be secured, of the number of incident photons to the pixel array unit is 3440 (128×128×0.21). When correction by the Poisson distribution is added, a dynamic range may be improved by about one digit.

Next, an output rate of data from the imaging element 110 will be described. From the imaging element 110, 128 rows of pixels are read by two lines at once, and thus, 256 (bit) binaries are output simultaneously. Since readout of one line is 5 µs, the data output rate is 51 Mbps (256 bit/5 µs (5×10$^{-6}$ second)). This data output rate is a rate with which even a system using a general central processing unit (CPU) can receive data from great number of imaging elements simultaneously and perform parallel processing sufficiently.

When a counter is provided to the output circuit (see the output circuit 118 of FIG. 3) of the imaging element 110 and in a case where only the total value of counts is output when each round of readout in the pixel array as a whole is completed (readout of one frame ends), a data rate of the output becomes extremely low.

Performance of the imaging element 110, which is assumed in the descriptions above is estimated roughly with reference to performance in a current general CMOS image sensor, with a certain degree of margin. Generally, in a CMOS image sensor, a signal from a pixel is read after a line to be read is serially switched, and thus, there is minimum time required before the next readout. Thus, in a general light detection, a photon counter using a semiconductor imaging chip such as a CMOS imaging sensor has very low time-resolution of light detection in each pixel operation and is much inferior to photomultiplier tube.

However, in the light detection apparatus 10 of the first embodiment of the present technique, distribution of the photon incidence is made uniform and random by the light uniformizing unit 200, and the photons are emitted randomly and uniformly to the great number of pixels integrated in a plane-shape. Thus, for example, while photon count is performed on all photons, incident to a single light receiving plane, only with time-resolution in a counter head including a photomultiplier tube, those are uniformly shared by great number of pixels in the light detection apparatus 10. As a result, it can be secured, by the light uniformizing unit 200, that incidence frequency of a photon to one pixel becomes quite low. Thus, the count accuracy and the dynamic range of the light detection apparatus 10 becomes higher than count accuracy and a dynamic range of the photomultiplier tube. That is, in the light detection apparatus 10, spatial resolution of the light receiving plane can compensate the low time-resolution equivalently. Especially, in the light detection apparatus 10, a determination device (the determination circuit 113) is mounted to a semiconductor imaging chip (the imaging element 110) and the amount of incident light to each pixel is digitally determined. Thus, it becomes possible to integrate several tens of thousands to several million of pixels, and the count accuracy and the dynamic range of the light detection apparatus 10 exceeds those of the photomultiplier tube.

The time-resolution (detection speed) can also be improved, for example, by increase in the speed of an AD conversion circuit, high parallelization in which lines of three systems or more are selected simultaneously and processed in parallel, or super-high parallelization in which a three dimensional structure is used (see, for example, JP 2011-71958 A). By improving the time-resolution, the unit exposure period is shortened without desensitization. Thus, the average number of photons incident to one pixel can be further reduced and the count accuracy and the dynamic range can be further improved.

Moreover, when fluorescence detection is performed rapidly, great number of photons become incident together to the light receiving plane in a short period of time between the excitation light pulse emission timing and the timing of the fluorescence attenuation. In the conventional fluorescence scanner for an imaging plate, including a photomultiplier tube in the counter head, it is difficult to count each of the great number of incident photons, which become incident together, only with the time-resolution. Thus, in the conventional fluorescence scanner for an imaging plate, including the photomultiplier tube in the unter head, the great number of photons which become incident together are detected together. That is, the output of the photomultiplier tube is treated as an analog pulse, and is digitalized by an external AD conversion device (see FIG. 8A in the following). Scintillation detection, in which one photon of a radiation generates great number of photons simultaneously, is in a similar manner. On the other hand, when the present technique is used, photon counting to respectively count the great number of photons, which become incident together, is possible and fluorescence detection with super-high accuracy becomes possible.

[Example of Effect]

Figure 8A:
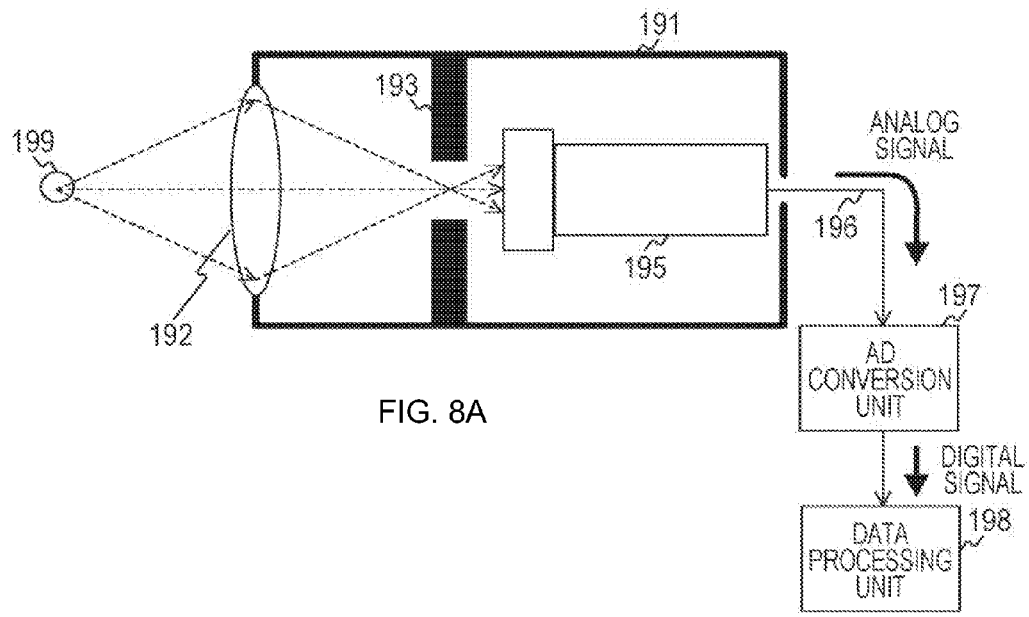
FIG. 8A and FIG. 8B are views schematically illustrating an example of a conventional detection head (detection head 191) to which a photomultiplier tube is applied and an example of the detection head (detection head 101) to which the light detection apparatus 10 of the first embodiment of the present technique is applied, respectively.
Figure 8B:
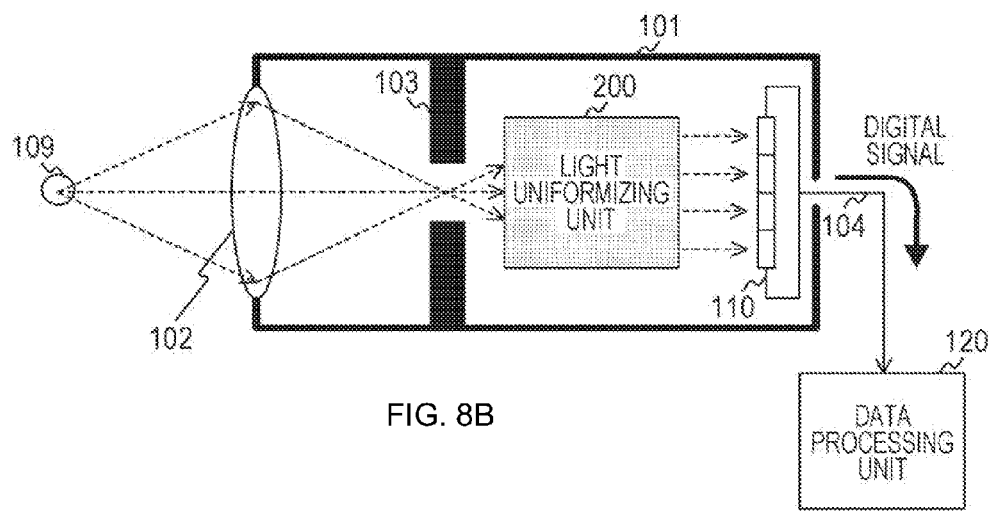

FIG. 8A and FIG. 8B are views schematically illustrating an example of the detection head (detection head 101) to which the light detection apparatus 10 of the first embodiment of the present technique is applied and an example of a conventional detection head (detection head 191) to which a photomultiplier tube is applied.

In FIG. 8A, an example of the detection head 191 to which the conventional photomultiplier tube is applied is illustrated. The detection head 191 includes a condensing lens 192, a pinhole 193, a photomultiplier tube 195, an AD conversion unit 197, and a data processing unit 198. In addition, a detection spot 199 is illustrated in the left side of the condensing lens 192. Also, the condensing lens 192 and the pinhole 193 are respectively similar to the condensing lens 102 and the pinhole 103 illustrated in FIG. 2, and thus, a description thereof is omitted here.

The photomultiplier tube 195 amplifies, by an electron avalanche, the electron generated by the photoelectric conversion, and outputs the amplified result as an analog pulse. The photomultiplier tube 195 requires high voltage for speeding up the electron in order to amplify the electron. The photomultiplier tube 195 supplies the generated analog pulse (analog signal) to the AD conversion unit 197 through a signal wire 196.

The AD conversion unit 197 digitally converts the analog pulse supplied by the photomultiplier tube 195, and outputs as a digital value of each sample section. The AD conversion unit 197 supplies the digital value to the data processing unit 198.

The data processing unit 198 calculates intensity of the light to be detected based on the digital value supplied by the AD conversion unit 197. For example, the data processing unit 198 adds up the digital values output by the AD conversion unit 197 in a determined sample period, and the added result is the fluorescence intensity of the detection spot 199.

In this manner, in the conventional detection head (detection head 191), the photomultiplier tube is used. Since the photomultiplier tube is expensive, the conventional detection head becomes expensive. Also, since high voltage is necessary, an apparatus to supply the high voltage is also needed. Furthermore, since the photomultiplier tube outputs the analog pulse, the AD conversion unit 197 is needed. Moreover, it is necessary to design the detection head with consideration for the analog pulse being transmitted.

In FIG. 8B, an example of the detection head (detection head 101), to which the light detection apparatus 10 according to the first embodiment of the present technique is applied, is illustrated. The detection head 101 illustrated in FIG. 8B is similar to that illustrated in FIG. 2, and thus, a detailed description thereof is omitted here.

As illustrated in FIG. 8B, since the light uniformizing unit 200 is included, photons become incident uniformly and randomly to each pixel of the imaging element 110. Thus, as illustrated in FIG. 6, it becomes possible to count photons, whereby photon counting can be easily performed.

Also, as illustrated in FIG. 8B, the imaging element 110 outputs a signal of a digital value (digital signal). In this manner, since the digital signal is output, there is less impact of noise, compared to the analog signal.

[Operation Example of Light Detection Apparatus]

Next, an operation performed by the light detection apparatus 10 when photon counting is performed in the first embodiment of the present technique will be described with reference to the drawings.

FIG. 9 is a flowchart illustrating an example of a processing procedure in a case where the light detection apparatus 10 of the first embodiment of the present technique performs a photon counting operation.

First, light, number of photons of which is to be detected (object of photon counting), becomes incident to the light uniformizing unit 200 of the detection unit 100 (step S901). Then, distribution of the light incident to the light uniformizing unit 200 is uniformized by the light uniformizing unit 200 (step S902). Subsequently, the uniformized light becomes incident to the pixel array unit 300 of the imaging element 110, and then, digital determination of the number of photons incident to the pixel is performed, by the determination circuit 113, for each pixel based on the accumulated signal of each pixel (step S903). Step S902 is an example of a light uniformizing step described in claims. Also, step S903 is an example of a determination step described in claims.

Next, determination values, each of which is a result value of the digital determination of each pixel, are summed by a frame as a unit and the number of photons of the light, the number of photons of which is to be detected, is calculated by the counting unit 130 (step S904). Then, after step S904, the processing procedure of the photon counting operation ends. Step S904 is an example of a calculation step described in claims.

In this manner, according to the first embodiment of the present technique, by providing the light uniformizing unit 200, light in which photons are distributed uniformly can be emitted to the pixel array unit 300 of the imaging element 110. That is, by providing the light uniformizing unit 200, the light suitable for the photon counting (light in which photons are distributed uniformly) can be provided to the imaging element. Thus, according to the first embodiment of the present technique, accuracy of photon counting can be improved.

2. Second Embodiment

In the first embodiment of the present technique, the description has been made on the assumption that all of the pixels in the pixel array unit is suitable for photon counting. However, actually, it is difficult to form all of the pixels in a CMOS image sensor as pixels having uniform quality. For example, a pixel having high leakage current (dark current) slightly generated even in a dark state is not suitable for photon counting.

Thus, in the second embodiment of the present technique, an example, in which count of the pixel having high dark current is made invalid (masked) to improve accuracy of photon counting, will be described with reference to FIG. 10 to FIG. 12.

[Example of Relationship Between Size of Dark Current and Number of Pixels]

Figure 10:
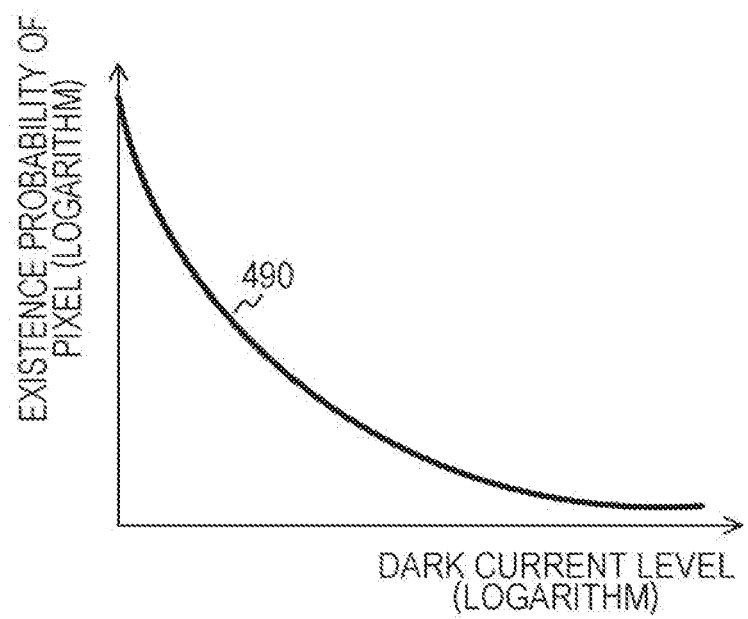
FIG. 10 is a view schematically illustrating a relationship between the size of dark current (dark current level) generated in a pixel 310 of a second embodiment of the present technique and the number of pixels 310 (existence probability of pixel).

FIG. 10 is a view schematically illustrating a relationship between the size of dark current (dark current level) generated in a pixel 310 of the second embodiment of the present technique and the number of the pixels 310 (existence probability of pixel).

In FIG. 10, a characteristic (characteristic 490), which indicates a relationship between the size of a dark current level and existence probability of pixels, is illustrated with the horizontal axis as an axis to indicate dark current level (logarithm) and the vertical axis as an axis to indicate existence probability of pixels (logarithm).

Here, dark current will be described. In the pixel 310, generally, leakage current (dark current) is generated slightly even in a dark state. For example, when there is a recombination center formed by an impurity or the like in the vicinity of a cathode terminal of a photodiode 311, the leakage current corresponding to the size of recombination center is generated therethrough. Also, the leakage current is generated in a case where charge leakage is generated, during a period of a readout operation, in floating diffusion (FD 322 of FIG. 2) in a floating state. In photon counting, the leakage current (dark current) becomes a dark count, which is counted even when there is no photon incidence, and causes deterioration in detection accuracy.

It is known that the dark current varies a lot from a pixel to a pixel. In a chart illustrated in FIG. 10, this characteristic of variation is illustrated. The characteristic 490 illustrated in this chart indicates the number of pixels generated at each dark current level. That is, as indicated in the characteristic 490, the number of pixels (existence probability) having almost no leakage current is the greatest. Then, the number of pixels (existence probability) becomes smaller as the leakage current becomes greater. For example, when a degree of dark current in the imaging element 110 is the leakage of an average around 0.5 electron per a pixel, most of the leakage is caused in about 10% of pixels having high dark current and bad performance.

Here, a relationship between the imaging element 110 according to the embodiments of the present technique and the pixel having high dark current level will be described. After uniformized by the light uniformizing unit 200, the light (fluorescence) from an object to be detected is emitted to each pixel in the pixel array unit 300 of the imaging element 110. Since the light to be detected is uniformized by the light uniformizing unit 200, arrangement (distribution state) of the pixel having high dark current level in the pixel array unit 300 does not have impact on the detection result. Thus, only the number of pixels having high dark current level becomes a problem.

For example, in a case where the upper limit of a percentage of the count values which is allowed to be corrected is 10%, when the percentage of the pixels having high dark current level is 10% or less of all of the pixels, dark counts can be reduced greatly by ignoring (invalidating) the count values of the pixels having high dark current levels. Since it is only to ignore the count values of the pixels having high dark current levels, the dark counts can be greatly reduced without worsening a range or accuracy of the detection.

Here, a case where the number of all the pixels (number of effective pixels) of the pixel array unit 300 is M, and the number of pixels having dark current levels lower than a predetermined standard is N will be described. In this case, first, positions of N pixels are detected before photon counting, and information related to the positions (positional information of mask pixel) is recorded into the counting unit 130. When photon counting is performed, count values of the N pixels, positions of which has been recorded, is invalidated (masked) and the number of photons received in one frame (in one exposure period) is calculated. That is, count values of all pixels in the pixel array unit 300 are summed with results of binary determination of these pixels as "0", and the number of photons received in a unit exposure period is calculated.

The percentage of the masked pixels (N) to the number of effective pixels M is known, the number of photons received in a unit exposure period can be corrected. This correction can be made, for example, by multiplying the total number of counts by M/(M−N).

In this manner, by specifying positions of the pixels which have high dark current levels and are not suitable for photon counting, and by invalidating (masking) results of binary determination of the pixels, it is possible to reduce dark counts greatly. Thus, even when there is a pixel having a high dark current level in the pixel array unit 300, even extremely weak luminescence can be detected accurately.

[Operation Example of Light Detection Apparatus in Detecting Pixel Having High Dark Current Level]

Next, in the second embodiment of the present technique, an operation (detecting operation of pixel to be masked) performed by a light detection apparatus 10 when a pixel having a high dark current level (high dark current pixel) is detected and a position thereof is recorded will be described with reference to the drawings.

Figure 11:
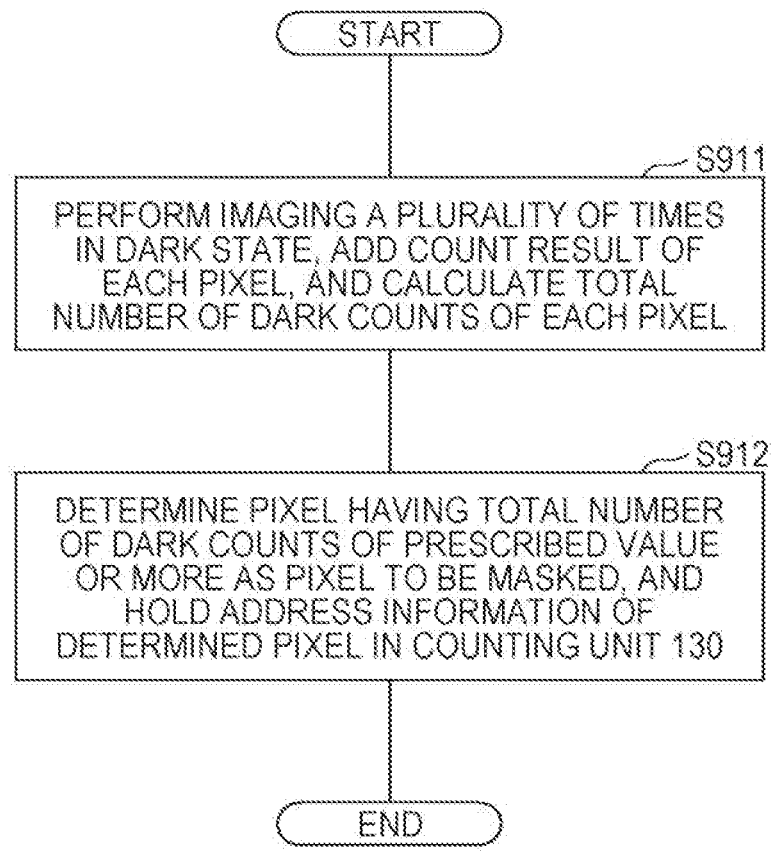
FIG. 11 is a flowchart illustrating an example of a detection processing procedure when a light detection apparatus 10 of the second embodiment of the present technique performs an operation of detecting a pixel to be masked.

FIG. 11 is a flowchart illustrating an example of a detection processing procedure when the light detection apparatus 10 of the second embodiment of the present technique performs an operation of detecting a pixel to be masked.

First, imaging in a dark state is performed a plurality of times (for example, 1000 times) and count results in the plurality of times of imaging of each pixel are added, whereby total number of dark counts is calculated for each pixel (step S911). In this detection, for example, to tighten a measurement condition, imaging is performed in around 60° C. (the higher temperature is, the higher dark current becomes) with an accumulation period having 33 ms being provided.

Next, a pixel having total number of dark counts of a prescribed value (threshold value) or more is determined as a high dark current pixel (pixel to be masked), and address information of the determined pixel is held in the counting unit 130 (step S912). For example, when the number of effective pixels is 128 lines×128 rows, about 2 k bites of a memory region is provided in the counting unit 130. A pixel address and a memory address are made to have one-to-one correspondence. To a determined high dark current pixel, "1" is recorded and to a normal pixel, "0" is recorded.

When the detection and the recording of high dark current pixels end in step S912, the detection processing procedure ends.

In FIG. 11, an example of holding the information related to a position of a pixel to be masked (positional information of mask pixel) in the counting unit 130 has been described, but it is not limited thereto. The positional information of a mask pixel only needs to be prepared before the performance of photon counting.

Thus, for example, it may be considered that the detecting operation of a pixel to be masked is performed in an inspection before shipping of a semiconductor imaging chip (the imaging element 110) and the detected result is recorded in a non-volatile memory provided in the semiconductor imaging chip. In this case, a data processing unit 120 (for example, fluorescence inspection system) to perform data processing of a signal from the imaging element 110 obtains the mask pixel positional information from the semiconductor imaging chip before performing the photon counting and copies the obtained information into a memory inside a system and uses the information.

Also, for example, during power activation (during start-up) of an apparatus (for example, fluorescence inspection system) to which the light detection apparatus 10 is provided, the detecting operation of a pixel to be masked may be performed in a state in which excitation light is not emitted, and the mask pixel positional information may be generated by the performance. Note that in this case, a function to perform a detecting operation of a pixel to be masked may be included as one of an operation mode in the semiconductor imaging chip, and a function in which the imaging element 110 obtains an address of the pixel to be masked and gives notice of the obtained address to the data processing unit may be provided.

[Operation Example of Light Detection Apparatus in Counting Pixel Having High Dark Current Level being Masked]

Next, in the second embodiment of the present technique, an operation (photon counting operation including masking) performed by the light detection apparatus 10 when a pixel having a high dark current level (high dark current pixel) is masked and photons are counted, will be described with reference to the drawings.

Figure 12:
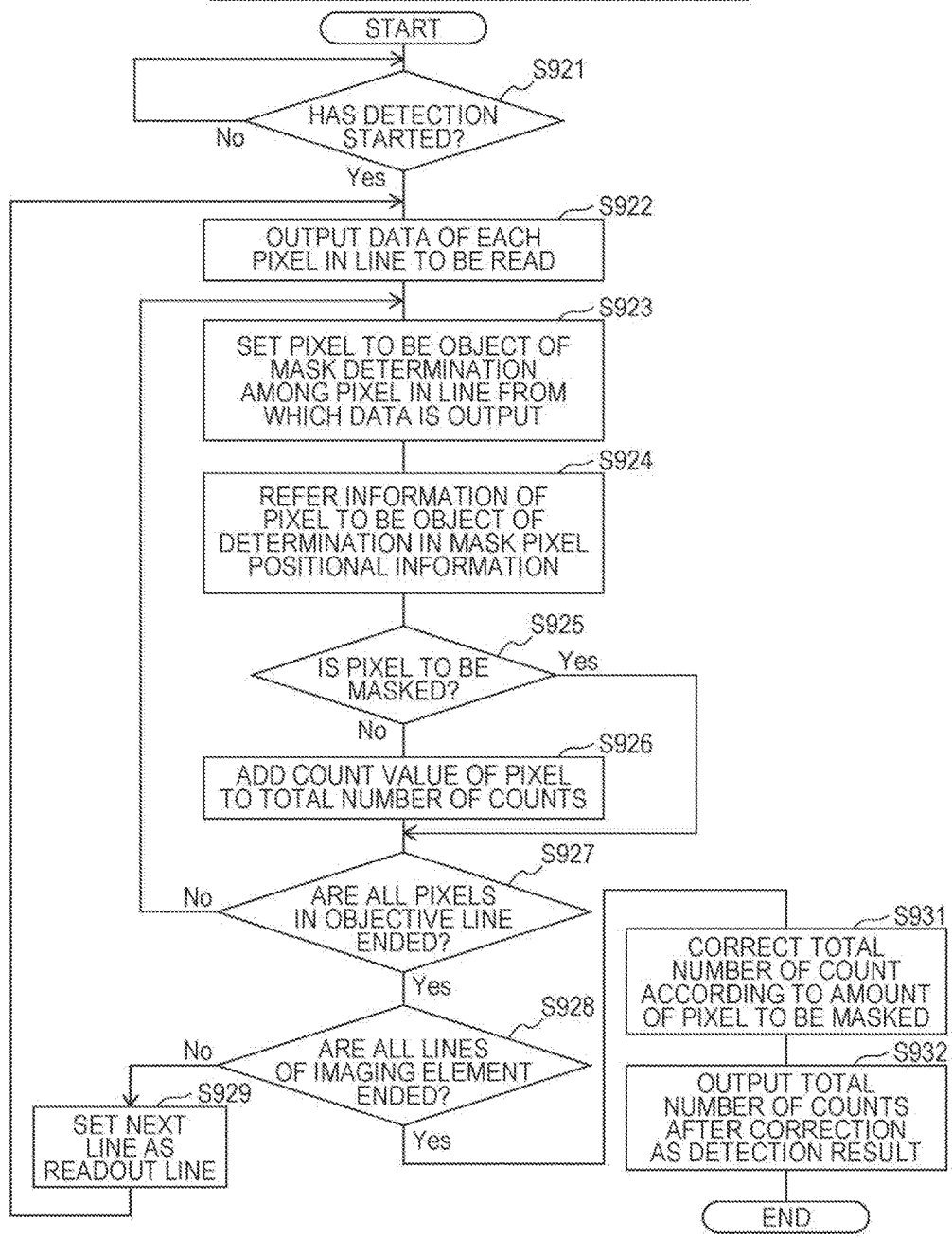
FIG. 12 is a flowchart illustrating an example of a processing procedure in a case where the light detection apparatus 10 of the second embodiment of the present technique performs a photon counting operation including masking.

FIG. 12 is a flowchart illustrating an example of a processing procedure in a case where the light detection apparatus 10 of the second embodiment of the present technique performs a photon counting operation including masking.

First, it is determined whether to perform detection of a photon by using the imaging element 110 (step S921) and when determined not to perform, the imaging element 110 is in a standby state until the performance.

On the other hand, when it is determined to perform detection of a photon (step S921), a result of binary determination (digital value) of each pixel of a line to be read (object line) in the imaging element 110 is output in such a state in which an address of the pixel can be identified (step S922). For example, when two lines are selected in one readout, existence or non-existence of photon incidence in each pixel in the two lines is output as a stream of binary data.

Subsequently, a pixel to be an object of mask determination (pixel to be determined) is set, by the counting unit 130, among the pixels in the line, results of the binary determination thereof being output (step S923). Then, based on an address of the set pixel to be determined, mask pixel positional information is referred to, and information, which indicates whether the pixel to be determined is a pixel to be masked, is referred to by the counting unit 130 (step S924).

Then, it is determined by counting unit 130 whether the pixel to be determined is a pixel to be masked (step S925).

When it is determined that it is a pixel to be masked, processing proceeds to step S927.

On the other hand, when it is determined that it not a pixel to be masked (step S926), a result of the binary determination ("0" or "1") of the pixel to be determined is added to the total number of counts (photon count value of one frame). By skipping step S926 and moving to step S927 in a case where it is determined that it is a pixel to be masked, mask processing (masking), in which a result of the binary determination of a pixel to be masked is invalidated, is performed.

Subsequently, it is determined by the counting unit 130 whether all pixels in the object line have been determined whether they are pixels to be masked (step S927). When it is determined that determination has not been performed on all pixels in the object line yet (step S927), processing returns to step S923 and a pixel to be determined is newly set from the pixels which has not been determined yet.

On the other hand, when it is determined that all pixels in the object line have been determined that they are pixels to be masked (step S927), it is determined by the counting unit 130 whether the determination of a pixel to be masked has been performed on all lines of pixels of the imaging element 110 (step S928). When it is determined that the determination has not performed on all lines yet (step S928), a next line is set as a line for readout (step S929). Then, after step S929, processing returns to step S922 and output of a result of the binary determination from the imaging element 110 and determination of a pixel to be masked are performed repeatedly. In this manner, the determination of a pixel to be masked is performed on pixels in one frame, and integration of results of the binary determination of normal pixels (pixel not to be masked) is performed.

Also, when it is determined that the determination of a pixel to be masked has been performed on all lines (step S928), correction of the total number of counts, which is performed corresponding to the number of pixels to be masked, is performed by the counting unit 130 (step S931). For example, as illustrated in FIG. 10, this correction is performed by multiplying the total number of counts by M/(M−N), according to a ratio of the number of pixels to be masked N to all the number of effective pixels M.

Then, the corrected total number of counts is output as a detected result of the photon counting (step S932) and the processing procedure of a photon counting operation including masking ends.

In this manner, according to the second embodiment of the present technique, by masking a pixel having high dark current, accuracy of photon counting can be improved.

In FIG. 12, only the correction of the total number of counts based on the number of pixels to be masked has been assumed as the correction of the total number of counts in the description, but correction is not limited thereto. By performing correction of the count value according to the Poisson distribution after the correction based on the number of pixels to be masked, accuracy of a detection result (total number of count) of photon counting can be further improved. As described in FIG. 6, since the object light is emitted uniformly and randomly to the pixel array unit 300 by the light uniformizing unit 200, the average number of photons can be calculated by count probability (total number of counts/number of effective pixels). Also, by calculating the total number of counts based on the average number of photons and the number of effective pixels, the total number of counts, in which count loss is corrected, can be calculated.

In this case, since having been corrected in step S931, substantial decrease of the number of effective pixels due to masking can be ignored.

In the second embodiment of the present technique, an example of performing count by the counting unit 130 of the data processing unit 120 has been described, but the embodiment is not limited thereto. For example, when a counter is provided in the imaging element 110 (in a semiconductor imaging chip) and only a total value of counts is output for readout of each frame, all the steps of the processing procedure of a photon counting operation including masking is performed in the imaging element 110. Also in this case, by making it possible to perform the correction of a count value according to Poisson distribution in the semiconductor imaging chip, accuracy of the detection result of photon counting can be further improved.

3. Third Embodiment

In the first and second embodiments of the present technique, an example, in which there is one pixel array unit including 128 lines×128 rows of pixels in an imaging element, has been described. An imaging element, which includes such a pixel array unit including small number of pixels, is quite small (for example, 2 mm square). Thus, compared to wafer working process, mounting process may become relatively expensive, in semiconductor manufacturing. Therefore, in an apparatus to which a plurality of detection apparatuses (detection head) is mounted, mounting becomes easy by lining up a plurality of pixel array units, to which a drive circuit and a readout circuit are provided, on the imaging element and by mounting them at once.

Thus, in the third embodiment of the present technique, an example, in which a plurality of pixel array units is provided on an imaging element, will be described with reference to FIG. 13 to FIG. 15.

[Example of Imaging Element Including a Plurality of Pixel Array Units]

Figure 13:
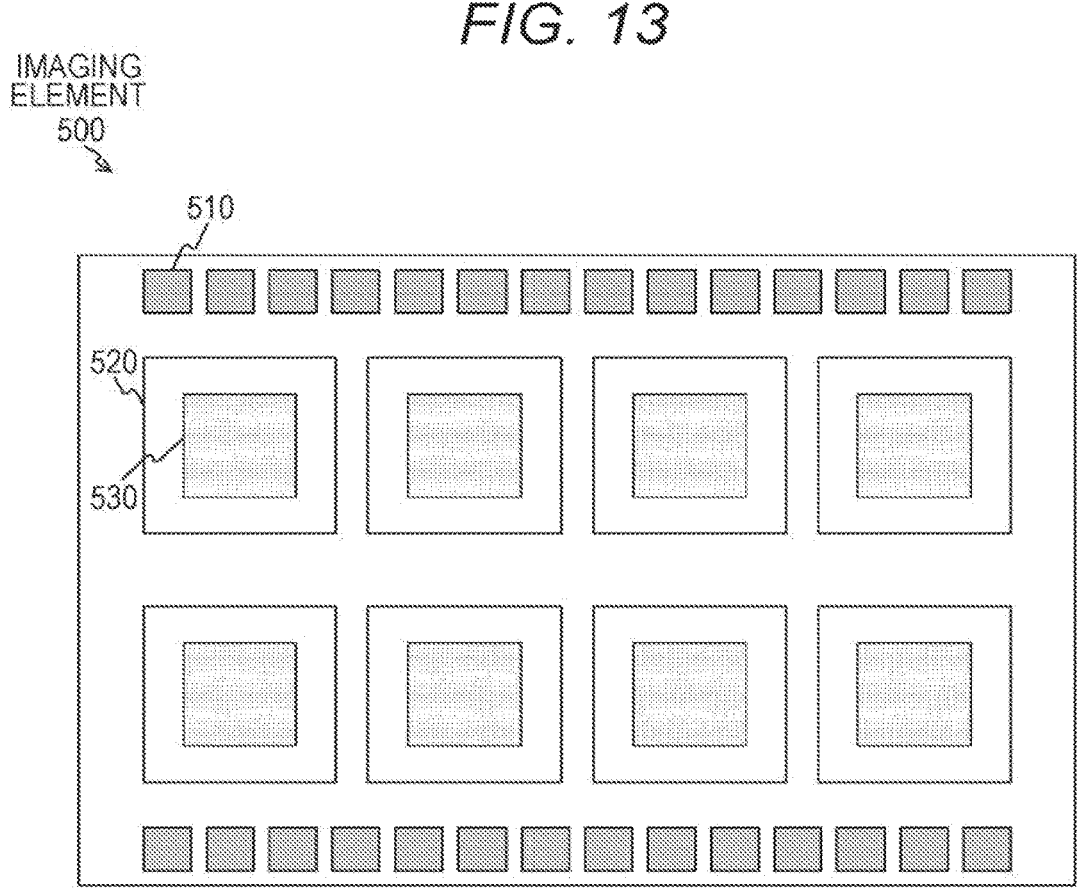
FIG. 13 is a conceptual diagram illustrating an example of an imaging element (imaging element 500) including a plurality of pixel array units according to a third embodiment of the present technique.

FIG. 13 is a conceptual diagram illustrating an example of an imaging element (imaging element 500) including a plurality of pixel array units according to the third embodiment of the present technique.

In FIG. 13, a top view of the imaging element 500 will be described on the assumption of XY axes in which a vertical direction is a Y-axis and a horizontal direction is an X-axis.

In the imaging element 500 illustrated in FIG. 13, eight circuits, each of which is a circuit illustrated in the imaging element 110 of FIG. 3 (hereinafter referred to as an imaging circuit 520), are provided on a single semiconductor imaging chip (the imaging element 500). That is, in the imaging element 500, eight pixel array units (see the pixel array unit 300 of FIG. 3), each of which is independently driven, are provided.

Also, to each of the eight imaging circuit 520, a light uniformizing unit 530 is provided.

In the imaging element 110, a pad (pad 510) to exchange signals with an external apparatus is arranged at the ends of the imaging element 110 (in FIG. 13, upper side and lower side). For example, an input pad of a power source and a synchronizing signal is wired to be shared by the eight imaging circuits 520. Pieces of digital data (bit stream of result of binary determination) generated by the eight imaging circuits 520 are wired to different pads to be output respectively from independent pads. In this case, the eight imaging circuits 520 operate simultaneously in parallel, and count results of photons are output from output pads respectively corresponding to the imaging circuits 520.

Next, an example of a module (an imaging module), which includes a semiconductor imaging chip (the imaging element 500) described in FIG. 13, will be described with reference to FIG. 14.

[Example of Imaging Module]

Figure 14:
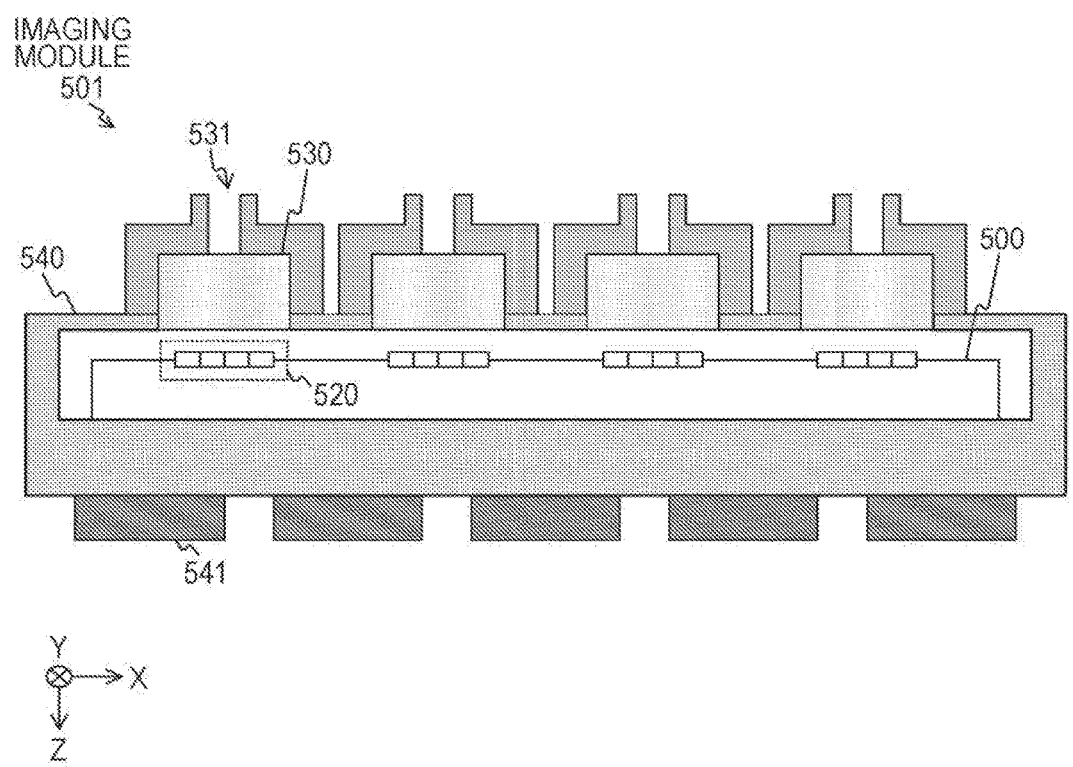
FIG. 14 is a schematic view illustrating an example of a module (imaging module 501) to which the imaging element (imaging element 500) including a plurality of imaging circuits is mounted.

FIG. 14 is a schematic view illustrating an example of a module (an imaging module 501) to which the imaging element (imaging element 500) including a plurality of imaging circuits is mounted.

In FIG. 14, a sectional view of the imaging module 501 will be described with a vertical direction as a Z-axis and a horizontal direction as an X-axis.

In FIG. 14, the imaging module 501 to which the imaging element 500 is mounted by a land grid array (LGA) type package is illustrated. Since the package is an LGA package, pads (a pad 541) are arranged in lattice-form on a bottom surface of the package (package 540) and the pads 541 and pads 510 of the imaging element 500 are connected to each other through lead wires.

Also, in the package 540, open windows (connectors 531) are respectively provided to the plurality of imaging circuits 520, and the light uniformizing units 530 are respectively provided between the connectors 531 and the imaging circuits 520. To the connector 531, an optical fiber can be welded. Light of an object to be detected can be guided to the light uniformizing unit 530 by the optical fiber.

For example, each of the imaging circuits 520 of the imaging module 501 illustrated in FIG. 14 can be used as a detection unit of each of detection heads of an apparatus which detects a plurality of detection spots simultaneously.

Also, each of the imaging circuits 520 of the imaging module 501 illustrated in FIG. 14 can be used to make light from one detection spot branch in a substantially uniform manner and to perform parallel detection. In this case, when count values of the eight imaging circuits 520 are added up, a dynamic range of imaging becomes octuple. That is, the maximum number of photons which can be detected simultaneously becomes 131072 (128×128×8). Thus, linear gradation output of 14 bits to 15 bits can be obtained without count correction using the Poisson distribution.

Next, an example of a detection head, which makes light from one detection spot branch in a substantially uniform manner and performs parallel detection, will be described with reference to FIG. 15.

[Structure Example of Detection Head]

Figure 15:
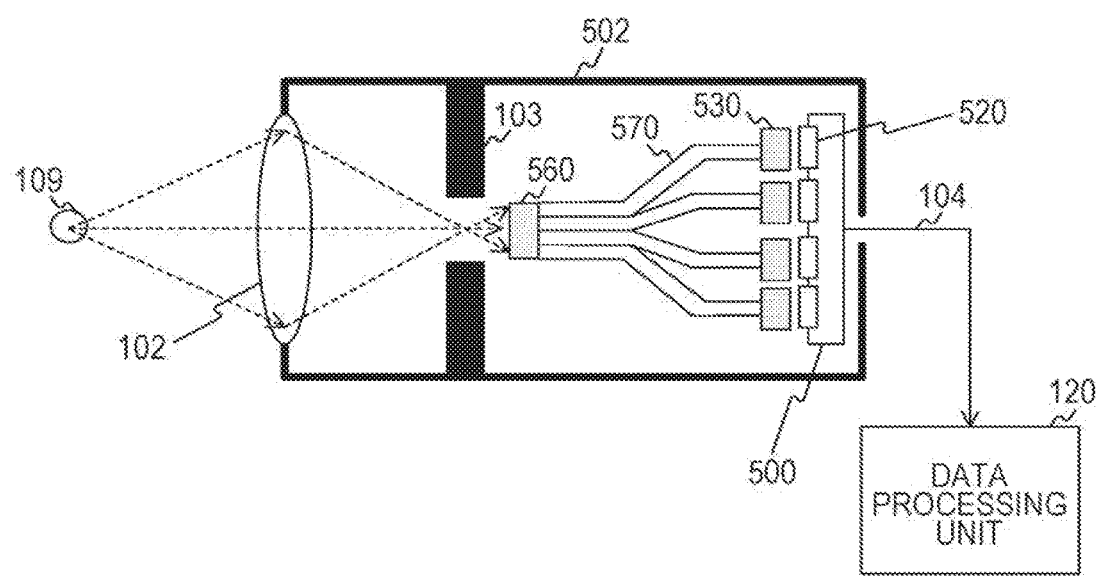
FIG. 15 is a conceptual diagram illustrating an example of a detection head (detection head 502) to which the imaging module 501 according to the third embodiment of the present technique is applied.

FIG. 15 is a conceptual diagram illustrating an example of a detection head (detection head 502) to which the imaging module 501 according to the third embodiment of the present technique is applied.

The detection head 502 includes a condensing lens 102, a pinhole 103, a light uniformizing unit 560, an optical fiber 570, the light uniformizing unit 530, the imaging circuit 520, and the imaging element 500. The detection head 502 is a modified example of the detection head 101 illustrated in FIG. 2, and thus, the same reference sign is given to what is the same with FIG. 2 and a description thereof is omitted here. Also, in FIG. 15, a package of the imaging module 501 is not illustrated. As the imaging module 501, the light uniformizing unit 530, the imaging circuit 520, and the imaging element 500 are illustrated.

In the detection head 502, a light uniformizing unit (the light uniformizing unit 560) of a first stage is provided to a place where light from a detection spot 109 reaches after passing through the pinhole 103. Then, on an output side of the light uniformizing unit 560, the plurality of optical fibers (the optical fiber 570) is connected. The optical fibers 570 are respectively connected to the plurality of light uniformizing units 560 provided to the imaging circuit 520.

Here, a description will be made focusing on the light uniformizing units 560 and the optical fibers 570.

Similarly to the light uniformizing unit 200 illustrated in FIG. 2, the light uniformizing units 560 substantially uniformize distribution of incident light (light to be the object of photon counting). The light uniformizing units 560 supply the substantially uniformized light to the connected plurality of optical fibers 570. That is, the same number of photons is supplied to the plurality of optical fibers 570. The light uniformizing units 560 are examples of a dividing unit described in claims.

The optical fibers 570 emit the light, which is uniformized by the light uniformizing unit 560, to the imaging circuits 520 on the imaging element 500. The plurality of optical fibers 570 is connected to the output side of the light uniformizing units 560, whereby the light uniformized by the light uniformizing unit 560 is equally divided into a plurality of pieces.

Then, pieces of branch light guided by the optical fibers 570 are substantially uniformized by the light uniformizing unit (light uniformizing unit 530) of a second stage and respectively emitted to the corresponding imaging circuits 520.

When the optical fibers 570 include functions to uniformize light, the light uniformizing unit (light uniformizing unit 530) arranged closely to the imaging circuits 520 can be omitted.

The plurality of imaging circuits 520 of the detection head 502 are driven simultaneously in parallel since a power source or a synchronizing signal is shared. When the result of binary determination is output from the imaging element 500, in the data processing unit 120, mask processing, adding, and count correction which have been described in the first and second embodiments of the present technique are performed on each of the eight imaging circuits 520. Then, the count values of the eight imaging circuits 520 are added up, and thus, the count value of the incident light from the detection spot is calculated.

In this manner, according to the third embodiment of the present technique, a plurality of imaging circuits (imaging unit) can be provided on one imaging element (single semiconductor imaging chip). Thus, since a plurality of imaging units can be easily provided, improvement of a dynamic range and the like become easy and accuracy of photon counting can be improved.

4. Fourth Embodiment

In the third embodiment of the present technique, an example in which eight imaging circuits operate simultaneously in parallel has been described, but the embodiment is not limited thereto. When operations of the eight imaging circuits are driven separately, different exposure periods can be set to the eight imaging circuits. That is, by enhancing a driving method, use of the detection head can be further expanded.

Thus, in the fourth embodiment of the present technique, an example of improving time-resolution by separating the eight imaging circuits into a plurality of groups and setting exposure periods in such a manner that the groups are exposed in different timing will be described with reference to FIG. 16 to FIG. 18.

Figure 16:
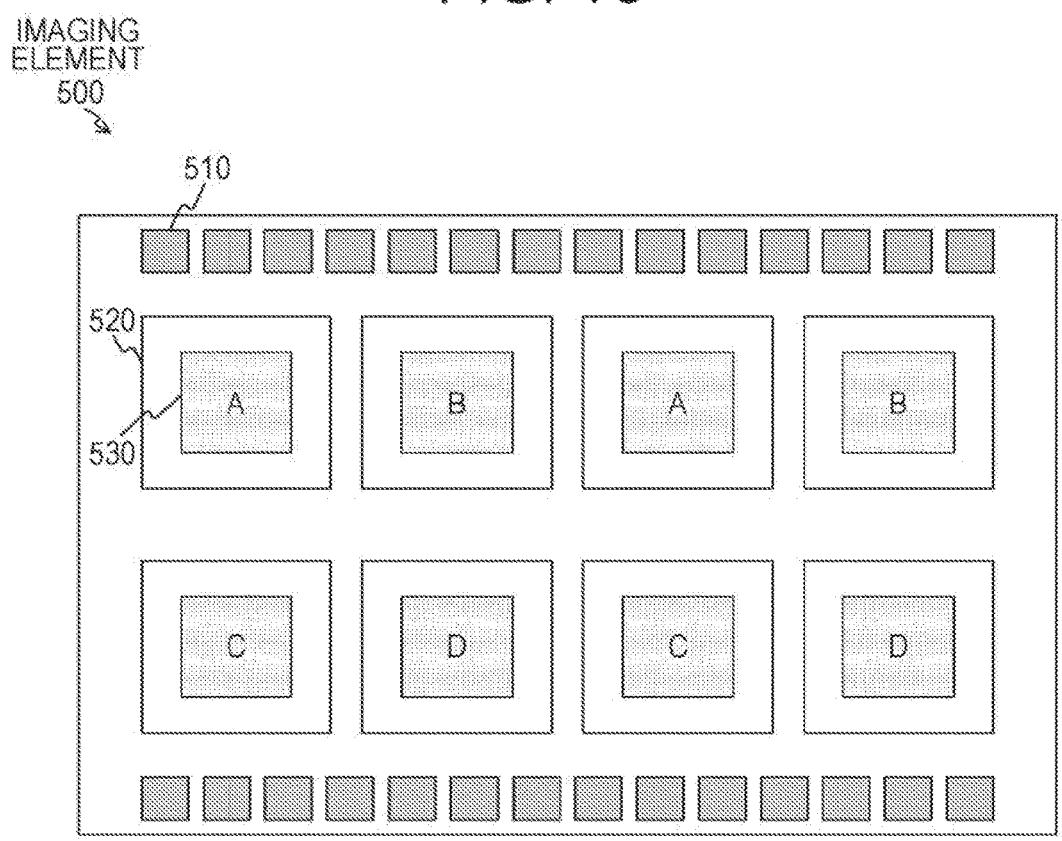
FIG. 16 is a conceptual diagram illustrating an example of separation, into four groups, of imaging circuits of an imaging element (imaging element 500) according to a fourth embodiment of the present technique.
Figure 18:
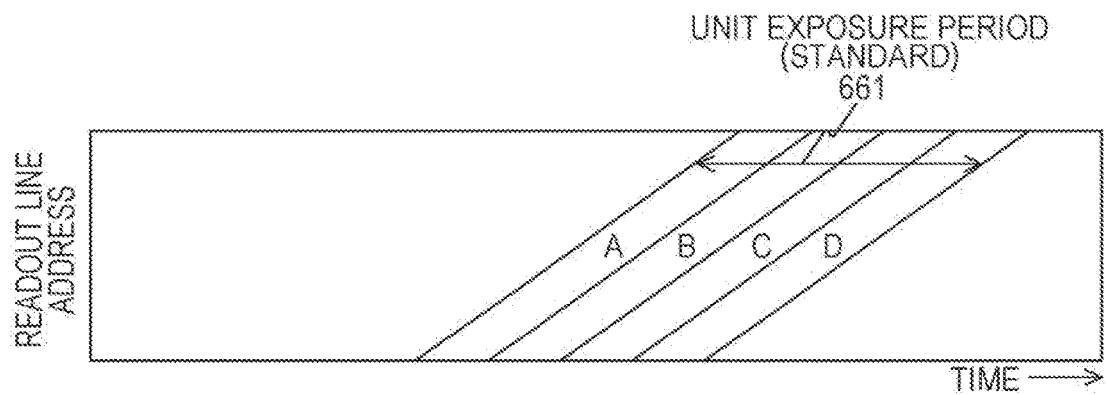
FIG. 18 is a view schematically illustrating an example of an effect of performing photon counting by separating the imaging circuits 520 into four groups in the fourth embodiment of the present technique.

In FIG. 16 to FIG. 18, an example of setting exposure periods by separating the imaging circuits of the imaging element (imaging element 500) described in the third embodiment of the present technique into four groups will be described.

[Example of Grouping of Imaging Circuits]

FIG. 16 is a conceptual diagram illustrating an example of separation, into four groups, of imaging circuits of the imaging element (imaging element 500) according to the fourth embodiment of the present technique.

In FIG. 16, an imaging element 500 which is similar to that of FIG. 13 is illustrated. Also, in FIG. 16, signs (A, B, C, and D) which indicate groups are assigned to the light uniformizing units 530 respectively provided to the imaging circuits 520 to indicate four groups of the imaging circuits (imaging circuit 520).

As illustrated in the imaging element 500 of FIG. 16, in the fourth embodiment of the present technique, the eight imaging circuits 520 are equally separated into a total of four groups (A, B, C, and D). That is, in the fourth embodiment of the present technique, one group is formed by two imaging circuits, and the imaging circuits 520 are driven separately by a group as a unit.

Next, an example, in which an exposure operation and a readout operation are set to each of the groups, will be described with reference to FIG. 17A to FIG. 17D.

[Example of Exposure Operation and Readout Operation of Imaging Element 110]

FIG. 17A to FIG. 17D are views schematically illustrating examples of an exposure operation and a readout operation of each group of the imaging circuits 520 separated into four groups in the fourth embodiment of the present technique.

In FIG. 17A and FIG. 17B, for convenience of description, timing to read a signal is referred to as "n" th readout timing and timing to read a preceding signal is referred to as "n−1" th readout timing in the description of FIG. 17.

In FIG. 17A, an exposure operation and a readout operation of the imaging circuits 520 in A-group is illustrated with a horizontal direction as a direction to indicate a time axis and a vertical direction as a direction to indicate a line (readout line address) from which a signal is read. In FIG. 17A, "n−1" th readout timing (readout timing (n−1) 621) and "n" th readout timing (readout timing (n) 622) of the imaging circuits 520 in A-group are illustrated. Also, in FIG. 17A, a standard exposure period (unit exposure period (standard) 624), which is not shortened or extended and is described in FIG. 7A to FIG. 7D, is illustrated. Also, in FIG. 17A, reset timing 623, which is timing to reset a photodiode and to remove electrons accumulated in the photodiode, is illustrated.

Similarly to FIG. 17A, in FIG. 17B, an exposure operation and a readout operation of the imaging circuits 520 in B-group are illustrated. Also, in FIG. 17C, an exposure operation and a readout operation of the imaging circuits 520 in C-group are illustrated, and in FIG. 17B, an exposure operation and a readout operation of the imaging circuits 520 in D-group are illustrated. The timing and the periods illustrated in FIG. 17B to FIG. 17D correspond to those illustrated in FIG. 17A, and thus, a description thereof is omitted.

Here, the exposure operations and the readout operations of the imaging circuits 520 in A-group to D-group will be described. First, common operations will be described with reference to FIG. 17A. The imaging circuits 520 set the reset timing 623 in such a manner that a period which is ¼ of the unit exposure period (standard) 624 becomes an exposure period, and reset accumulation of photons in the photodiode at this timing. That is, the accumulation of photons in the photodiode is reset at timing (the reset timing 623) which is about ¾ of the unit exposure period (standard) 624 behind the readout timing (n−1) 621. Then, in a period (period of ¼ of unit exposure period (standard) 624) behind the reset timing 623 to the readout timing (n) 622, electrons are accumulated and are read as accumulated signals at the readout timing (n) 622. In this manner, in an exposure period which is ¼ of the standard unit exposure period, the imaging circuits 520 are driven to receive photons.

Next, difference between groups in respect to exposure operations and readout operations will be described. Similarly to the imaging circuits 520 in A-group, the imaging circuits 520 in B-group to D-group are also driven in such a manner that photons, which are accumulated in an exposure period of ¼ of the standard unit exposure period, become accumulated signals. However, timing of the ¼ exposure period (referred to as exposure period of group), in which the photons to be accumulated signals are received, is different from group to group.

The imaging circuits 520 in B-group are driven in such a manner that reset timing 633 becomes the same timing as the readout timing (n) 622 of A-group. Also, readout timing (n) 632 of the imaging circuits 520 in B-group is the timing which is about ¼ of the unit exposure period behind the reset timing 633.

Also, a reset timing 643 of the imaging circuits 520 in C-group is the same timing as the readout timing (n) 632 of B-group. Readout timing (n) 642 is the timing which is about ¼ of the unit exposure period behind the reset timing 643.

Then, reset timing 653 of the imaging circuits 520 in D-group is the same timing with the readout timing (n) 642 of C-group. Readout timing (n) 652 is the timing which is about ¼ of the unit exposure period behind the reset timing 653.

In this manner, the eight imaging circuits 520 are driven in such a manner that the exposure periods of the groups do not overlap. Thus, there is no period in which photons are not detected, although the accumulated signals are generated with the photons being accumulated only for the time shorter than the unit exposure period.

Next, in FIG. 18, an effect of this driving will be described with reference to a view, in which the exposure periods of the four groups are lined up on a time axis.

[Example of Effect of Grouping]

FIG. 18 is a view schematically illustrating an example of an effect of performing photon counting by separating the imaging circuits 520 into four groups in the fourth embodiment of the present technique.

In FIG. 18, a view in which the exposure periods of the four groups (A, B, C, and D) illustrated in FIG. 17A to FIG. 17D are lined up on the same time axis, is illustrated.

As illustrated in FIG. 18, each of the exposure periods of the four groups is a quarter of the standard exposure period (unit exposure period (standard) 661) which is not shortened or extended.

Here, the number of counts of photon counting will be described. Since the eight imaging circuit 520 of the imaging element 500 are separated into four groups as illustrated in FIG. 16, two imaging circuits 520 belong to one group. Thus, when calculating the number of counts in the exposure period of each group, the counting unit 130 corrects the sum of the count values of the imaging circuits 520, which belong to the group, based on a ratio of the number of the imaging circuits 520 which belong to the group to the total number of the imaging circuits 520, and calculates the number of counts. That is, since the eight imaging circuits 520 are equally separated into four groups, the number of counts in the exposure period can be calculated by multiplying the sum of the count values of two imaging circuits 520 which belong to the same group by four.

For example, the number of counts in the exposure period of A-group is calculated by multiplying the sum of the count values of the two imaging circuits 520 in A-group by four. Also, the number of counts in the exposure period of B-group is calculated by multiplying the sum of the two imaging circuits 520 in B-group by four.

Since light is uniformized in the light uniformizing unit (light uniformizing unit 560 of FIG. 15) of the first stage and it is secured that substantially the same number of photons become incident to the eight imaging circuits, this correction can be performed accurately.

In this manner, according to the fourth embodiment of the present technique, by separating the eight imaging circuits into groups and driving the groups separately, time-resolution can be improved. That is, according to the fourth embodiment of the present technique, accuracy of photon counting can be improved.

5. Application Example of Present Technique

The light detection apparatus (imaging apparatus) according to the first to fourth embodiments of the present technique can be widely applied to conventional electronic devices to which a photomultiplier tube, an avalanche photodiode, a photodiode, or the like is provided. For example, the light detection apparatus (imaging apparatus) according to the first to fourth embodiments of the present technique can be applied to a fluorescence scanner of an imaging plate or a scintillation counter of a radiation. In addition, the light detection apparatus (imaging apparatus) according to the first to fourth embodiments of the present technique can also be applied to a detector of a DNA chip, an X-ray imaging apparatus which is called a digital radiography (DR), a computed tomography (CT) apparatus, a single photon emission tomography (SPECT) apparatus, or the like. Thus, examples of the electronic devices to which such a light detection apparatus is applied will be illustrated in FIG. 19 to FIG. 21.

[Application Example to Electronic Device]

Figure 19:
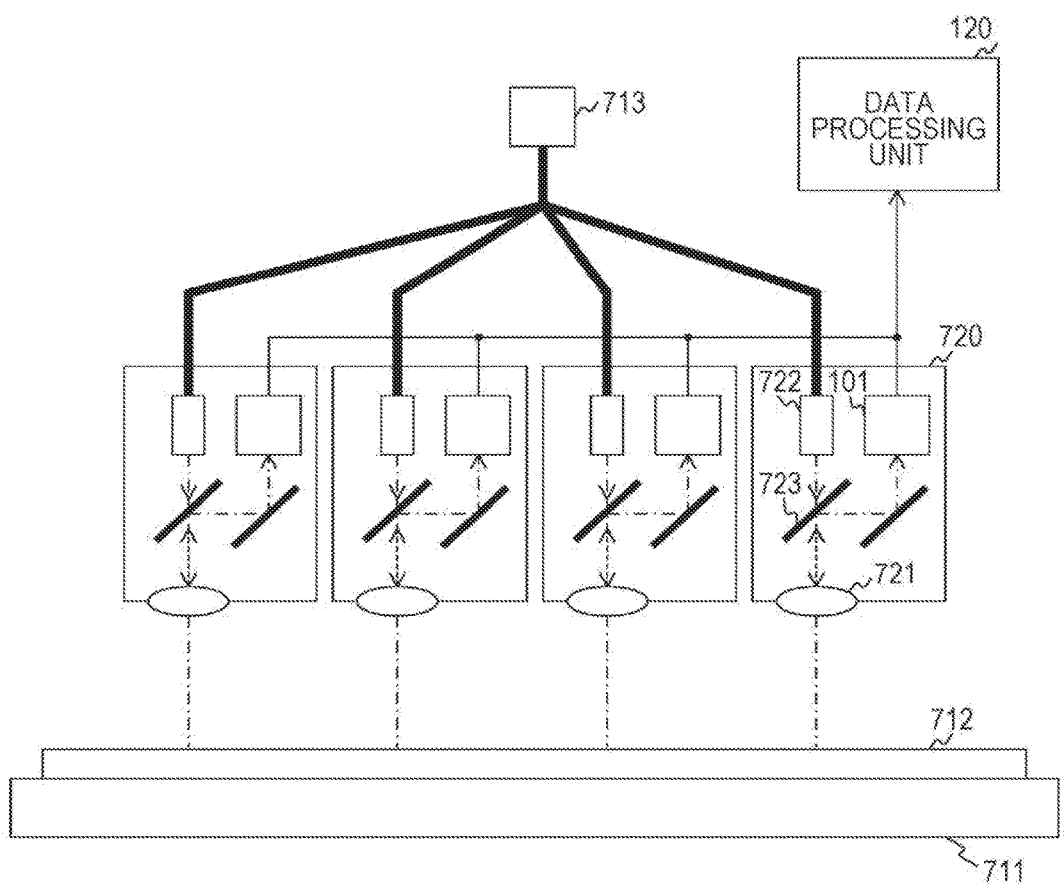
FIG. 19 is a schematic view illustrating an example of a fluorescence scanner which detects fluorescence of a plurality of spots in parallel by applying the embodiments of the present technique.

FIG. 19 is a schematic view illustrating an example of a fluorescence scanner which detects fluorescence of a plurality of spots in parallel by applying the embodiments of the present technique.

In FIG. 19, an inspection table 711, an inspection material 712, four detection modules 720, an excitation light source 713, and a data processing unit 120 are illustrated.

In FIG. 19, a description will be made on the assumption of a fluorescence scanner including an imaging plate as the inspection material 712. That is, the fluorescence scanner illustrated in FIG. 19 is an example in which a plurality of detection modules 720 are included to increase speed of the detection of photostimulated luminescence from the imaging plate.

Each of the detection module 720 includes an objective lens 721, an excitation light emitting unit 722, a beam splitter 723, and a detection head 101.

In each of the detection module 720, excitation light is emitted from the excitation light emitting unit 722. The excitation light passes through the beam splitter 723, and become incident to the objective lens 721. Then, the objective lens 721 narrows down (condense) the excitation light into a spot-shape and emits the excitation light to the inspection material 712. A position (focusing position), to which the most condensed excitation light becomes incident, on the inspection material 712 is the detection spot illustrated in the first to fourth embodiments of the present technique. Then, due to the excitation light, fluorescence is generated corresponding to the quantity of latent images of the X-ray.

Pieces of fluorescence, which are incident to the objective lens 721, of the fluorescence generated in the inspection material 712 are reflected by the beam splitter 723 and optical paths thereof are guided to become incident to the detection head 101. Then, the detection head 101 performs photon counting on the incident pieces of fluorescence.

In the fluorescence scanner illustrated in FIG. 19, four detection modules 720 are arranged. The excitation light is emitted simultaneously to the four detection spots, and fluorescence is detected in parallel. When simultaneous detection of the four spots ends, the inspection table 711 is moved for one spot by a stepper motor and next detection is performed.

In FIG. 19, an example of supplying the excitation light from the same light source (excitation light source 713) to the excitation light emitting unit 722 of each detection module has been illustrated. However, there may be an example of providing, to each detection module, a light source (such as light emitting diode (LED)) to generate excitation light. Note that for convenience of description, a band-pass filter in a midway of an optical path is omitted in the description, but by setting various band-pass filters at appropriate positions, accuracy of the detection is improved. For example, by providing a filter, which limits a band of the excitation light, to an excitation light emission opening of the excitation light source 713, probability of generating only objective fluorescence is improved. Also, by providing a filter, which allows only the wavelength of fluorescence to be transmitted, in an optical path from the beam splitter 723 to the detection head 101, background noise can be reduced.

In this manner, by applying the embodiments of the present technique to a fluorescence scanner, a plurality of detection heads can be easily provided. This is because a place (an imaging element 110) to detect the light in the detection head is a CMOS image sensor, it is possible to manufacture inexpensively in large quantities. That is, by applying the embodiments of the present technique to a fluorescence scanner, detection speed can be improved compared to that using an expensive photomultiplier tube.

Figure 20A:
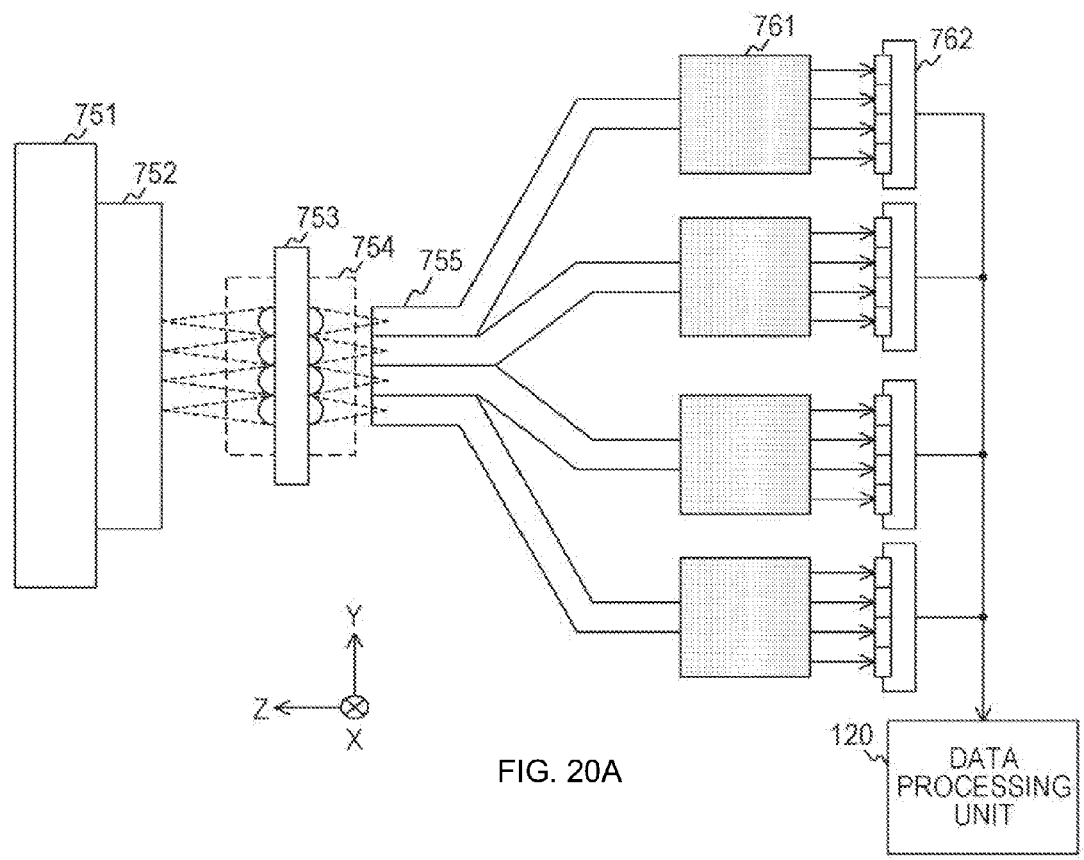
FIG. 20A and FIG. 20B are schematic views illustrating examples, which are different from the example of FIG. 19, of a fluorescence scanner which detects fluorescence of a plurality of spots in parallel by applying the embodiments of the present technique.
Figure 20B:
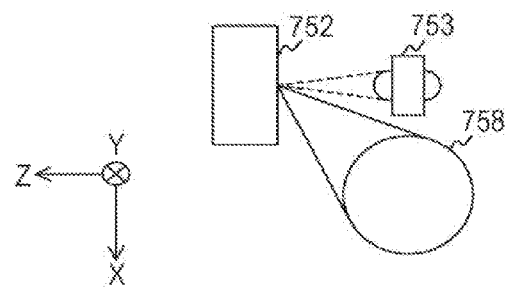

FIG. 20A and FIG. 20B are schematic views illustrating examples, which are different from the example of FIG. 19, of a fluorescence scanner which detects fluorescence of a plurality of spots in parallel by applying the embodiments of the present technique.

In FIG. 20A and FIG. 20B, an example of a fluorescence scanner to which the embodiments of the present technique are applied to perform a line scan is illustrated. The fluorescence scanner of FIG. 20 includes an inspection table 751, an inspection material 752 and a micro lens array 753. Also, the fluorescence scanner includes an excitation light emitting unit 754, an optical fiber 755, a light uniformizing unit 761, an imaging element 762, and a data processing unit 120. Note that in a description of FIG. 20A, it is assumed that a vertical direction is a Y-axis and a horizontal direction is a Z-axis in YZ axes. Also, in FIG. 20B, it is assumed that a vertical direction is an X-axis and a horizontal direction is a Z-axis in XZ axes, and a view in which the micro lens array 753 and the excitation light emitting unit 754 are focused is illustrated.

In the fluorescence scanner of FIG. 20, micro lenses are lined up in one line-shape in the micro lens array 753 (one line in a direction of Y-axis of FIG. 20A). Also, the excitation light emitting unit 754 is provided in parallel with the micro lenses lined up in a line-shape. The excitation light emitting unit 754 emits pieces of the excitation light at once to a condensing position (detection spot) of each of the plurality of micro lenses lined up in a line-shape in the micro lens array 753. A relationship between one micro lens in the micro lens array 753 and excitation light from the excitation light emitting unit 754 is illustrated in FIG. 20B in which XZ axes are assumed.

In the fluorescence scanner of FIG. 20, pieces of the excitation light are emitted at once to the plurality of detection spots (line-shaped inspection region), which correspond to a plurality of pixels lined up in a line-shape, of the inspection material 752 from the excitation light emitting unit 754 arranged in parallel with the micro lens array 753. The fluorescence generated at each detection spot (corresponding to detection pixel) is condensed by the micro lenses in the micro lens array 753. Then the condensed fluorescence becomes incident to the optical fibers 755 respectively corresponding to micro lenses and is guided to the light uniformizing units 761 to which the optical fibers 755 respectively correspond. Then, the fluorescence is substantially uniformized by the light uniformizing unit 761 and emitted, in a substantially uniform manner, to the pixel array units of the corresponding imaging element 762. As described in the first embodiment of the present technique, when the optical fiber 755 is an optical fiber including a light uniformizing function, the optical fiber 755 includes a function of the light uniformizing unit 761, and thus, the light uniformizing unit 761 can be omitted.

In this manner, by applying the embodiments of the present technique to a fluorescence scanner, it is possible to manufacture a fluorescence scanner, which can perform a line scan, inexpensively and to improve the detection speed.

Figure 21:
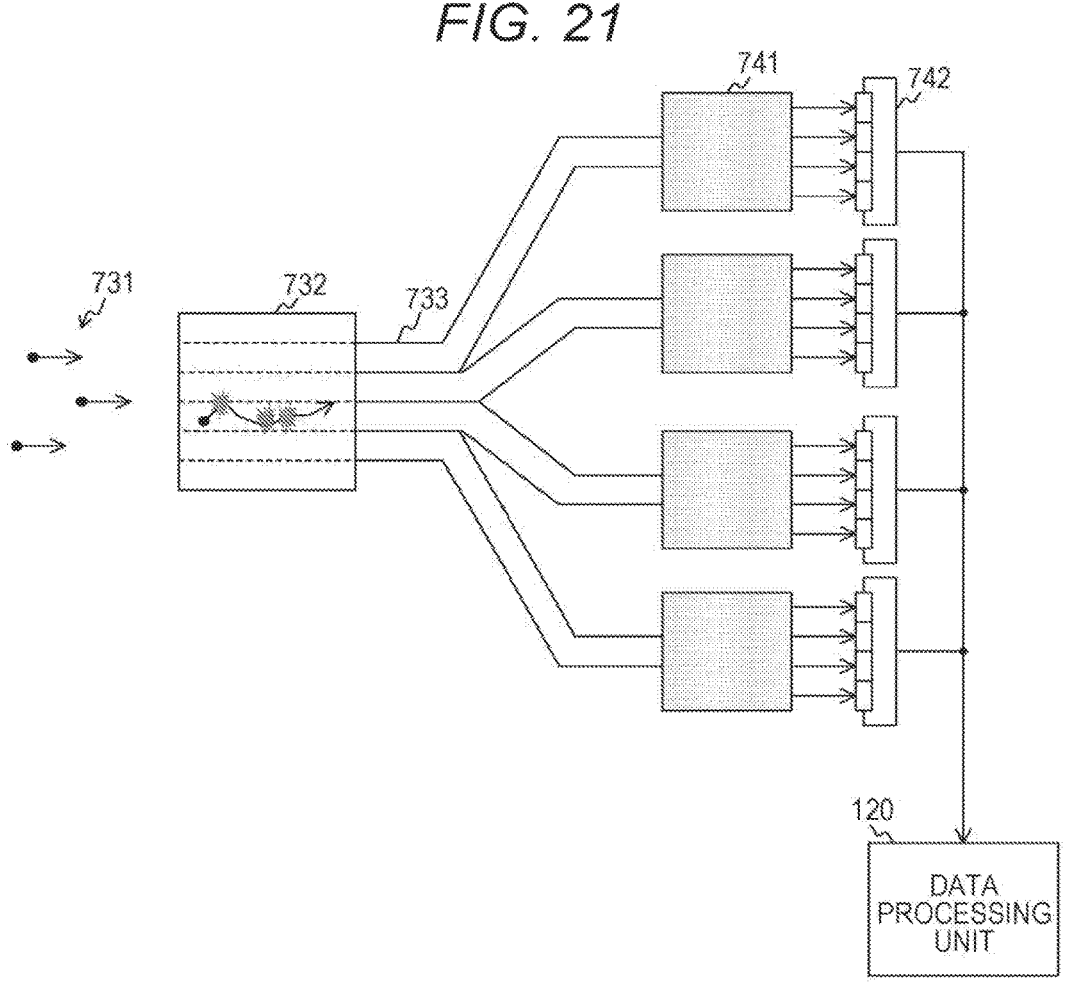
FIG. 21 is a schematic view illustrating an example in which the embodiments of the present technique are applied to a scintillation detector of an X-ray.

FIG. 21 is a schematic view illustrating an example in which the embodiments of the present technique are applied to a scintillation detector of an X-ray.

In FIG. 21, a scintillator 732, an optical fiber 733, a light uniformizing unit 741, and an imaging element 742 are illustrated.

When an X-ray (X-ray 731) becomes incident to the scintillator 732, a plurality of photons is generated substantially at the same time, according to energy intensity of the incident X-ray. To the scintillator 732, an optical fiber 733 (or a light guide) is connected by each detection unit (detection pixel unit in case of conventional photodiode detection). The photons incident to each detection unit are guided by the optical fiber 733 and reach the light uniformizing unit 741. Then, the photons are substantially uniformized and emitted, in a substantially uniform manner, to a pixel array unit of the imaging element 742. As described in the first embodiment of the present technique, when the optical fiber 733 includes a light uniformizing function, the light uniformizing unit 741 can be omitted since the optical fiber 733 includes the function of the light uniformizing unit 741.

In this manner, the embodiments of the present technique can be applied to a scintillation detector. For example, by introducing such a structure to a detector of a CT apparatus, it becomes possible to detect scintillation light much more sensitive than a conventional detector such as a photodiode, and to contribute to improvement of accuracy of detection or to reduction of radiation exposure due to decrease in the amount of the X-ray. In addition, a large external apparatus including an AD converter is not necessary, and thus, it becomes possible to make an apparatus smaller and more inexpensive. A similar structure can be introduced, for example, to SPECT or PET in which a conventional photomultiplier tube is used to detect gamma rays.

In FIG. 19 to FIG. 21, an example of the four imaging elements has been described. By using the imaging module (imaging module 501) of the third embodiment of the present technique, it is possible to make the imaging elements further smaller, lighter, and more inexpensive.

In this manner, by applying the embodiments of the present technique to electronic devices, great number of detection heads with an easy structure can be provided inexpensively. Thus, detection heads of the applied electronic device (such as fluorescence detection apparatus) can be made smaller and lighter easily. Also, since an external AD converter is not necessary, impact of noise on a signal can be reduced. Specifically, since a detection unit of light (imaging element) can be manufactured in semiconductor manufacturing process similar to that of a general CMOS image sensor, the detection unit of light (an imaging element) can be manufactured at extremely low price. That is, high parallelization of hundreds or thousands can be easily realized. Thus, for example, in a case of a fluorescence scanner, it is possible to secure high throughput by high parallelization, while improving resolution by making a detection spot smaller.

Note that there is an effect not only on the electronic device to which great number of detection heads are provided, but also, on an electronic device in which a single detection head is used. For example, by applying the present technique to a scintillation dosimeter of a radiation, a small and light pocket dosimeter having super-sensitive detection can be realized by using an inexpensive semiconductor imaging element.

In this manner, according to the embodiments of the present technique, by making the light, which is uniformized by the light uniformizing unit, incident to the imaging element, accuracy of photon counting can be improved.

Note that in the embodiments of the present technique, fluorescence detection is assumed in the description, but the embodiments of the present technique is not limited to the fluorescence and can be applied to various apparatuses which need to measure weak light. Specifically, in a field where high detection accuracy of light quantity is required, photon counting according to the embodiments of the present technique is quite effective, and photon counting having high accuracy can be inexpensively and easily realized. For example, recently, to detect difference in light absorption amount due to hemoglobin or blood-sugar by emitting near-infrared light of a particular band to a blood vessel and measuring the amount of reflected light is under development in a research to be applied to a man-machine interface or diabetes diagnosing. To a light detector in such a field, the application of the present technique is effective.

Note that the embodiments described above are examples to embody the present technique, and matters according to the embodiments and matters used to specify the invention according to claims correspond to each other. Similarly, the matters used to specify the invention according to claims and the matters according to the embodiments of the present technique, to which the same names are assigned, correspond to each other. However, the present technique is not limited to the embodiments thereof, and can be embodied by making various modifications to the embodiments within the scope thereof.

Also, the processing procedure described in the embodiments above can be seen as a method including a series of steps of the procedure, or also can be seen as a program to make a computer perform the series of steps of the procedure or a recording medium to store the program. As this recording medium, such as a hard disk, a compact disc (CD), a mini disc (MD), a digital versatile disk (DVD), a memory card, a Blu-ray Disc (registered trademark) can be used.

The present technique may also be embodied in the structures described below.

(1) An imaging apparatus including a light uniformizing unit configured to substantially uniformize distribution of incident light, which is incident to an imaging element in which a plurality of pixels is arranged and the number of photons of which is to be detected, in an orthogonal direction toward an optical axis and to supply the uniformized light to the imaging element.

(2) The imaging apparatus according to (1), further including a calculation unit, wherein, the imaging element performs digital determination in respect to the number of incident photons of the uniformized light supplied to each of the plurality of pixels and outputs a determination result value of the digital determination of each of the plurality of pixels, and the calculation unit sums the output determination result values of the plurality of pixels by a frame as a unit and calculates, based on the summed value, the number of photons of the incident light in an exposure period of the frame.

(3) The imaging apparatus according to (2), wherein the calculation unit calculates the number of photons of the incident light, based on the summed value, by using difference correction information indicating a relationship between the number of photons actually incident to the plurality of pixels and the summed value.

(4) The imaging apparatus according to (3), wherein the imaging element performs binary determination as the digital determination, and the calculation unit performs the calculation by using information, which is related to Poisson distribution or a relationship approximate to the Poisson distribution, as the difference correction information.

(5) The imaging apparatus according to any one of (2) to (4), wherein based on pixel positional information to identify a pixel having high dark current among the plurality of pixels, the calculation unit eliminates the determination result value of the pixel having high dark current and calculates the summed value.

(6) The imaging apparatus according to (5), wherein the calculation unit corrects the summed value based on a ratio of the number of pixels, the determination result values of which are eliminated, to the total number of pixels.

(7) The imaging apparatus according to (6), wherein the imaging element performs binary determination as the digital determination, and the calculation unit calculates the number of photons of the incident light, based on the corrected summed value, by using differential information related to Poisson distribution or a relationship approximate to the Poisson distribution.

(8) The imaging apparatus according to any one of (1) to (7), wherein the imaging element includes a plurality of pixel arrays, each of which is driven independently, and the light uniformizing units are respectively provided to and paired with the plurality of pixel arrays.

(9) The imaging apparatus according to (8), further including a dividing unit configured to substantially uniformize distribution of the incident light in an orthogonal direction of an optical axis and to divide the uniformized incident light into a plurality of pieces of incident light, wherein, the light uniformizing unit supplies, to the pixel array paired therewith, the incident light divided into a plurality of pieces.

(10) The imaging apparatus according to (9), further including a calculation unit, wherein, the plurality of pixel arrays have same length and same start timing of exposure periods, and each of the plurality of pixel arrays performs digital determination in respect to the number of incident photons of the light supplied to each of the plurality of pixels in the pixel array and outputs a determination result value of the digital determination of each of the plurality of pixels, and the calculation unit sums the output determination result values of the plurality of pixels by an exposure period as a unit, and calculates, based on the summed value, the number of photons of the incident light in the exposure period.

(11) The imaging apparatus according to (9), further including a calculation unit, wherein, the plurality of pixel arrays are separated into a plurality of groups having different start timing of exposure periods, and each of the plurality of pixel arrays performs digital determination in respect to the number of incident photons of the light supplied to each of the plurality of pixels in the pixel array and outputs a determination result value of the digital determination of each of the plurality of pixels, and the calculation unit sums the output determination result values of the plurality of pixels by a group as a unit and corrects the summed value based on a ratio of the number of pixel arrays which belong to the group related to the summed value to the total number of pixel arrays, and then, calculates, based on the corrected summed value, the number of photons of the incident light in an exposure period of the group.

(12) An electronic device including: a light uniformizing unit configured to substantially uniformize distribution of incident light, which is incident to an imaging element in which a plurality of pixels is arranged and the number of photons of which is to be detected, in an orthogonal direction toward an optical axis of the incident light and to supply the uniformized light; the imaging element configured to perform digital determination on each of the plurality of pixels in respect to the number of incident photons of the supplied light and to output a determination result value of the digital determination of each of the plurality of pixels; and a calculation unit configured to sum the output determination result values of the plurality of pixels by a frame as a unit and to calculate, based on the summed value, the number of photons of the incident light in an exposure period of the frame.

(13) A photostimulated luminescence detection scanner including a detection unit which includes a plurality of imaging units, each of the imaging unit including: a light uniformizing unit configured to substantially uniformize distribution of incident light, the number of photons of which is to be detected, in an orthogonal direction toward an optical axis and to supply the uniformized light; and an imaging element configured to perform digital determination on each of the plurality of pixels in respect to the number of incident photons of the supplied light and to output a determination result value of the digital determination of each of the plurality of pixels.

(14) An imaging method including: a light uniformizing step to substantially uniformize distribution of incident light, which is incident to an imaging element in which a plurality of pixels is arranged and the number of photons of which is to be detected, in an orthogonal direction toward an optical axis of the incident light and to supply the uniformized light to the imaging element; a determination step to perform digital determination on each of the plurality of pixels in respect to the number of incident photons of the light supplied to each of the plurality of pixels; and a calculation step to sum the determination result values of the plurality of pixels by a frame as a unit and to calculate, based on the summed value, the number of photons of the incident light in an exposure period of the frame.

REFERENCE SIGNS LIST

10 Light detection apparatus
100 Detection unit
101 Detection head
102 Condensing lens
103 Pinhole
110 Imaging element
120 Data processing unit
130 Counting unit
140 Recording unit
200 Light uniformizing unit

What is claimed is:

1. An imaging apparatus, comprising:
an imaging element which comprises a plurality of pixels; and
a light uniformizing unit configured to:
substantially uniformize distribution of a light for which a number of photons is detected; and
supply the uniformized light to the imaging element.

2. The imaging apparatus according to claim 1, wherein the light is incident in an orthogonal direction toward an optical axis of the imaging element.

3. The imaging apparatus according to claim 1, wherein the imaging element is configured to:
determine a result of a digital determination in respect to the number of photons of the uniformized light supplied to each of the plurality of pixels; and
output the determined result of the digital determination of each of the plurality of pixels.

4. The imaging apparatus according to claim 3, further comprising
a calculation unit configured to:
calculate sum of the determined result of the digital determination of each of the plurality of pixels based on a frame as a unit; and
calculate the number of photons of the light in an exposure period of the frame based on the sum.

5. The imaging apparatus according to claim 4, wherein the calculation unit is further configured to calculate the number of photons of the light based on difference correction information that indicates a relationship between the number of photons actually incident to the plurality of pixels and the sum.

6. The imaging apparatus according to claim 5, wherein the imaging element is further configured to determine a result of a binary determination as the result of the digital determination, and
the calculation unit is further configured to calculate the sum based on information related to Poisson distribution or a relationship approximate to the Poisson distribution as the difference correction information.

7. The imaging apparatus according to claim 4, wherein the calculation unit is further configured to:
eliminate the determined result of a pixel which comprises dark current lower than a standard; and
calculate the sum based on a pixel positional information to identify the pixel which comprises the dark current lower than the standard among the plurality of pixels.

8. The imaging apparatus according to claim 7, wherein the calculation unit is further configured to correct the sum based on a ratio of a number of pixels of which the determined result is eliminated to a total number of pixels.

9. The imaging apparatus according to claim 8, wherein the calculation unit is further configured to calculate the number of photons of the light based on the corrected sum and differential information related to Poisson distribution or a relationship approximate to the Poisson distribution.

10. The imaging apparatus according to claim 1, wherein the imaging element further comprises a plurality of pixel arrays, each of which is driven independently, and
the light uniformizing unit is paired with each of the plurality of pixel arrays.

11. The imaging apparatus according to claim 10, further comprising a dividing unit configured to:
substantially uniformize distribution of the light in an orthogonal direction of an optical axis of the imaging element; and
divide the uniformized light into a plurality of pieces of light,
wherein, the light uniformizing unit is further configured to supply the uniformized light divided into the plurality of pieces to a pixel array of the plurality of pixel arrays paired with the light uniformizing unit.

12. The imaging apparatus according to claim 10, wherein the plurality of pixels arrays have same length and same start time of exposure periods, and
an array of the plurality of pixel arrays is configured to:
determine a result of a digital determination in respect to the number of photons of the light supplied to each of the plurality of pixels in the array; and
output the determined result of the digital determination of each of the plurality of pixels in the array,
wherein the imaging apparatus further comprises a calculation unit configured to:
calculate sum of the determined result of each of the plurality of pixels in the array based on an exposure period as a unit; and
calculate the number of photons of the light in the exposure period based on the sum.

13. The imaging apparatus according to claim 10, wherein the calculation unit is further configured to:
calculate sum of the determined result of the plurality of pixels in the array based on a group as a unit;
correct the sum based on a ratio of a number of pixel arrays which belong to the group related to the sum to a total number of pixel arrays; and
calculate the number of photons of the light in an exposure period of the group based on the corrected sum,
wherein, the plurality of pixel arrays are separated into a plurality of groups which comprise different start time of exposure periods, and
wherein each of the plurality of pixel arrays is configured to:
determine the result of the digital determination in respect to the number of photons of the uniformized light supplied to each of the plurality of pixels in the pixel array; and
output the determined result of the digital determination of each of the plurality of pixels in the pixel array.

14. An electronic device, comprising:
an imaging element which comprises a plurality of pixels;
a light uniformizing unit configured to:
substantially uniformize distribution of a light for which a number of photons is detected; and
supply the uniformized light to the imaging element;
wherein the imaging element is configured to:

determine a result of a digital determination on each of the plurality of pixels in respect to the number of photons of the supplied light; and output the determined result of the digital determination of each of the plurality of pixels; and a calculation unit configured to:

calculate sum of the determined result of digital determination of each of the plurality of pixels based on a frame as a unit; and calculate the number of photons of the light in an exposure period of the frame based on the sum.

15. A photostimulated luminescence detection scanner, comprising:

a detection unit, wherein the detection unit comprises a plurality of imaging units, wherein each imaging unit of the plurality of imaging units comprises:

an imaging element which comprises a plurality of pixels; and a light uniformizing unit configured to:

substantially uniformize distribution of a light for which a number of photons is detected; and supply the uniformized light to the imaging element, wherein the imaging element is configured to:

determine a result of a digital determination in respect to the number of photons of the uniformized light supplied to each of the plurality of pixels; and output the determined result of the digital determination of each of the plurality of pixels.

16. The photostimulated luminescence detection scanner according to claim 15, further comprising a calculation unit configured to:

calculate sum of the determined result of the digital determination of each of the plurality of pixels based on a frame as a unit; and calculate the number of photons of the light in an exposure period of the frame based on the sum.

17. The photostimulated luminescence detection scanner according to claim 16, wherein the calculation unit is further configured to calculate the number of photons of the light based on difference correction information that indicates a relationship between the number of photons actually incident to the plurality of pixels and the sum.

18. The photostimulated luminescence detection scanner according to claim 17, wherein the imaging element is configured to determine a result of a binary determination as the result of the digital determination, and the calculation unit is further configured to calculate the sum based on information related to Poisson distribution or a relationship approximate to the Poisson distribution as the difference correction information.

19. The photostimulated luminescence detection scanner according to claim 16, wherein the calculation unit is further configured to:

eliminate the determined result of a pixel which comprises dark current lower than a standard; and calculate the sum based on pixel positional information to identify the pixel which comprises the dark current lower than the standard among the plurality of pixels.

20. An imaging method, comprising:

substantially uniformizing distribution of a light for which a number of photons is detected;

supplying the uniformized light to an imaging element which comprises a plurality of pixels;

determining a result of a digital determination on each of the plurality of pixels in respect to the number of photons of the uniformized light supplied to each of the plurality of pixels;

calculating a sum of the determined result of the plurality of pixels based on a frame as a unit; and calculating the number of photons of the light in an exposure period of the frame based on the sum.

* * * * *